US008491938B2

(12) United States Patent
Feng

(10) Patent No.: US 8,491,938 B2
(45) Date of Patent: Jul. 23, 2013

(54) POTENT INHIBITORY EFFECT OF ZINC IN COMBINATION WITH SULFORAPHANE ON CANCER CELL GROWTH

(75) Inventor: Pei Feng, Towson, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 488 days.

(21) Appl. No.: 12/690,432

(22) Filed: Jan. 20, 2010

(65) Prior Publication Data

US 2010/0183740 A1  Jul. 22, 2010

Related U.S. Application Data

(60) Provisional application No. 61/146,342, filed on Jan. 22, 2009.

(51) Int. Cl.

| | | |
|---|---|---|
| *A01N 59/16* | (2006.01) | |
| *A01N 43/04* | (2006.01) | |
| *A01N 55/02* | (2006.01) | |
| *A01N 31/00* | (2006.01) | |
| *A61K 33/32* | (2006.01) | |
| *A61K 31/70* | (2006.01) | |
| *A61K 31/315* | (2006.01) | |
| *A61K 31/095* | (2006.01) | |

(52) U.S. Cl.
USPC .............. 424/641; 514/24; 514/494; 514/706

(58) Field of Classification Search
USPC ..................... 424/641; 514/24, 494
See application file for complete search history.

(56) References Cited

U.S. PATENT DOCUMENTS

| 5,955,269 A * | 9/1999 | Ghai et al. .................... 435/6.11 |
|---|---|---|
| 2006/0269616 A1* | 11/2006 | Giampapa ..................... 424/641 |
| 2008/0248129 A1* | 10/2008 | Bartunek et al. ............. 424/630 |

OTHER PUBLICATIONS

National Cancer Institute: Breast cancer prevention retrieved online Aug. 7, 2007 from the internet http://www.cancer.gov/templates/doc.aspx?viewed=D972A74B-D25A-4F86-B8ED-33EB3C0450E4&version, p. 1 only.*
Medline Plus: Medical Encyclopedia: Ovarian cancer retrieved online on Aug. 9, 2007 from the internet https://www.nlm.nih.gov/medlineplus/ovariancancer.html (p. 1-3 and 5 only).*
National Cancer Institute: Breast Cancer Prevention retrieved online Aug. 7, 2007 from the internet http://www.cancer.gov/cancertopics/pdq/prevention/breast/Patient (p. 1-4).*
Hong et al. (Chem. Res. Toxicol. 2005: 18, 1917-1926).*
Rudolf et al. (Biofactors, 2005, 23(2):107-20-Abstract).*
Costello, L.C., and Franklin, R.B., Novel role of zinc in the regulation of prostate citrate metabolism and its implications in prostate cancer, The Prostate 1998, 35:285-296, Wiley-Liss, Inc., New York, NY.
Feng et al., The Involvement of Bax in Zinc-Induced Mitochondrial Apoptogenesis in Malignant Prostate Cells, Mol Cancer, Mar. 2008, 7:25, BioMed Central, United Kingdom.
Feng et al., Direct effect of zinc on mitochondrial apoptogenesis in prostate cells, The Prostate 2002, 52:311-318, Wiley-Liss, Inc., New York, NY.
Feng et al., Zinc induces mitochondria apoptogenesis in prostate cells, Mol Urol 2000, 4:31-36, Mary Ann Liebert, Inc., New Rochelle, New York.
Zhang et al., A major inducer of anticarcinogenic protective enzymes from broccoli: isolation and elucidation of structure, Proc Natl Acad Sci U S A 1992, 89:2399-2403, National Academy of Sciences, Washington, D.C.
Jin et al., Sulforaphane sensitizes tumor necrosis factor-related apoptosis-inducing ligand-mediated apoptosis through downregulation of ERK and Akt in lung adenocarcinoma A549 cells, Carcinogenesis 2007, 28:1058-1066, Oxford University Press, United Kingdom.
Kim et al., Sulforaphane sensitizes tumor necrosis factor-related apoptosis-inducing ligand (TRAIL)-resistant hepatoma cells to TRAIL-induced apoptosis through reactive oxygen species-mediated up-regulation of DR5, Cancer Res 2006, 66:1740-1750, American Association for Cancer Research, Philadelphia, PA.
Choi et al., D,L-Sulforaphane-induced cell death in human prostate cancer cells is regulated by inhibitor of apoptosis family proteins and Apaf-1, Carcinogenesis 2007, 28:151-162, Oxford University Press, United Kingdom.

* cited by examiner

*Primary Examiner* — Mina Haghighatian
*Assistant Examiner* — Helen Chui
(74) *Attorney, Agent, or Firm* — Nevrivy Patent Law Group P.L.L.C.

(57) ABSTRACT

This invention relates to compositions comprising zinc and sulforaphane which can be used in the treatment or prevention of cancer. The invention also relates to methods of treating or preventing cancer, including prostate cancer, which comprises the administration of zinc and sulforaphane to a patient in need thereof.

4 Claims, 14 Drawing Sheets

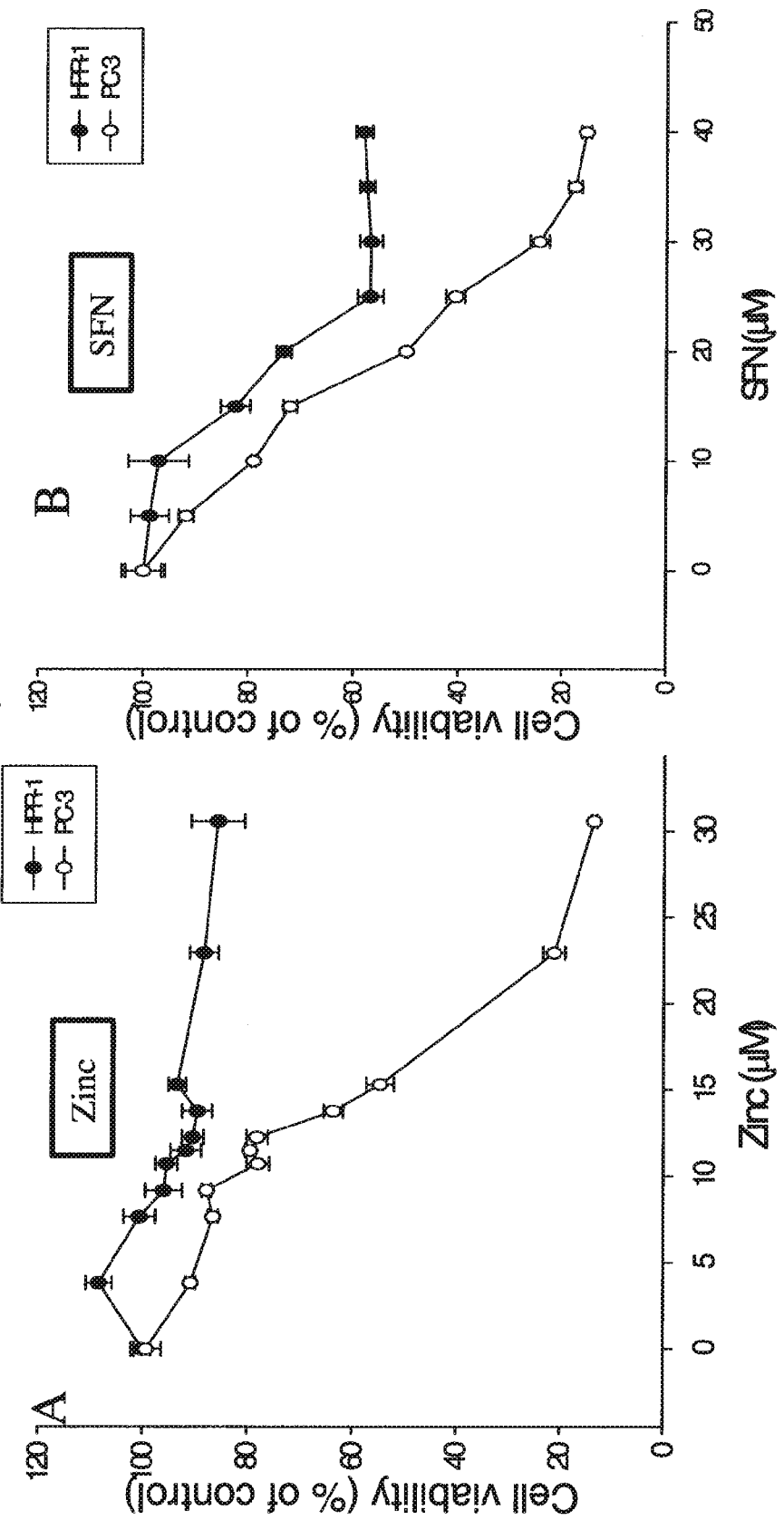
Fig. 1. Effect of zinc and SFN on viability of HPR-1 and PC-3 cells

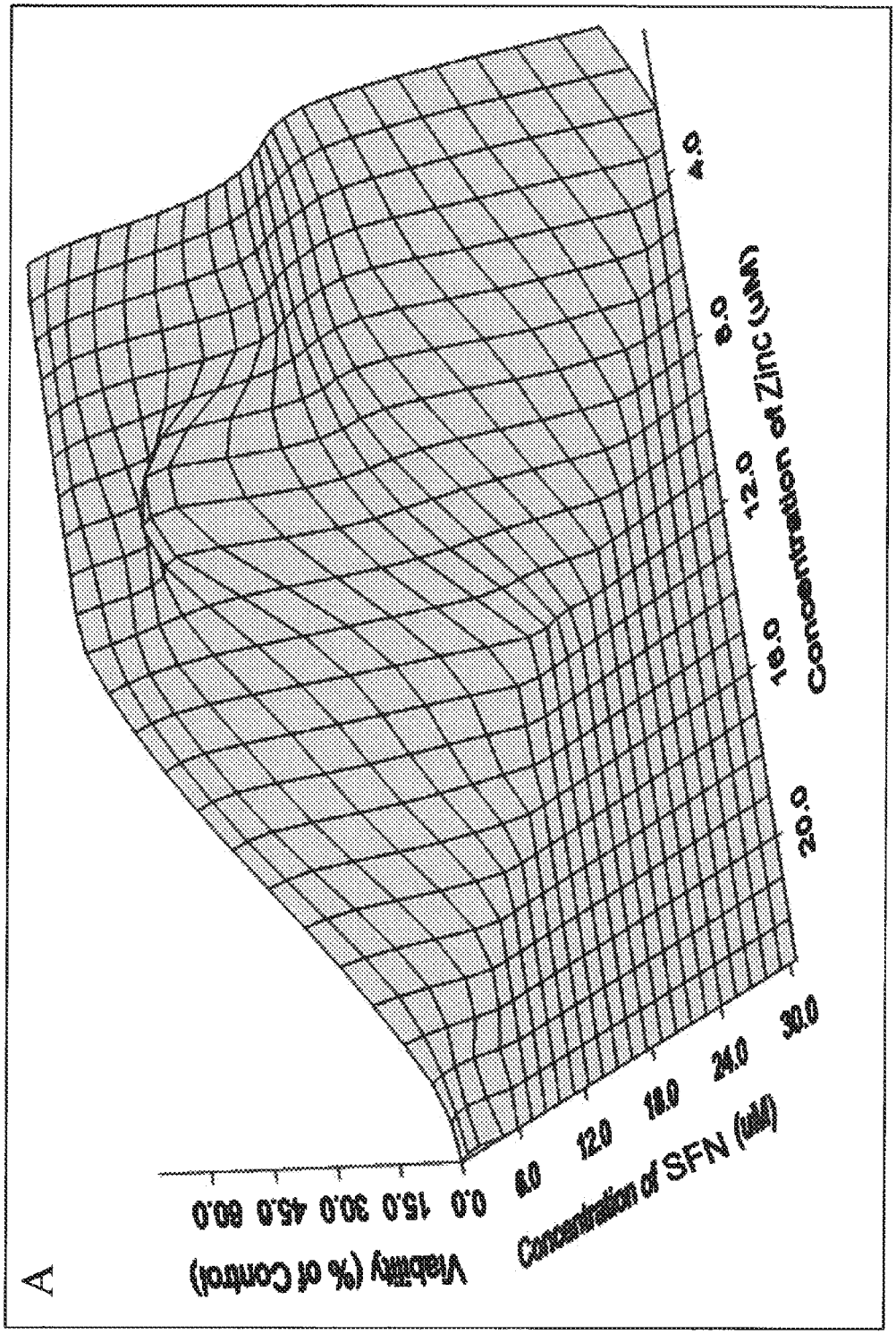
Fig. 2. Determination of combinational effect of zinc and SFN on PC-3 cells

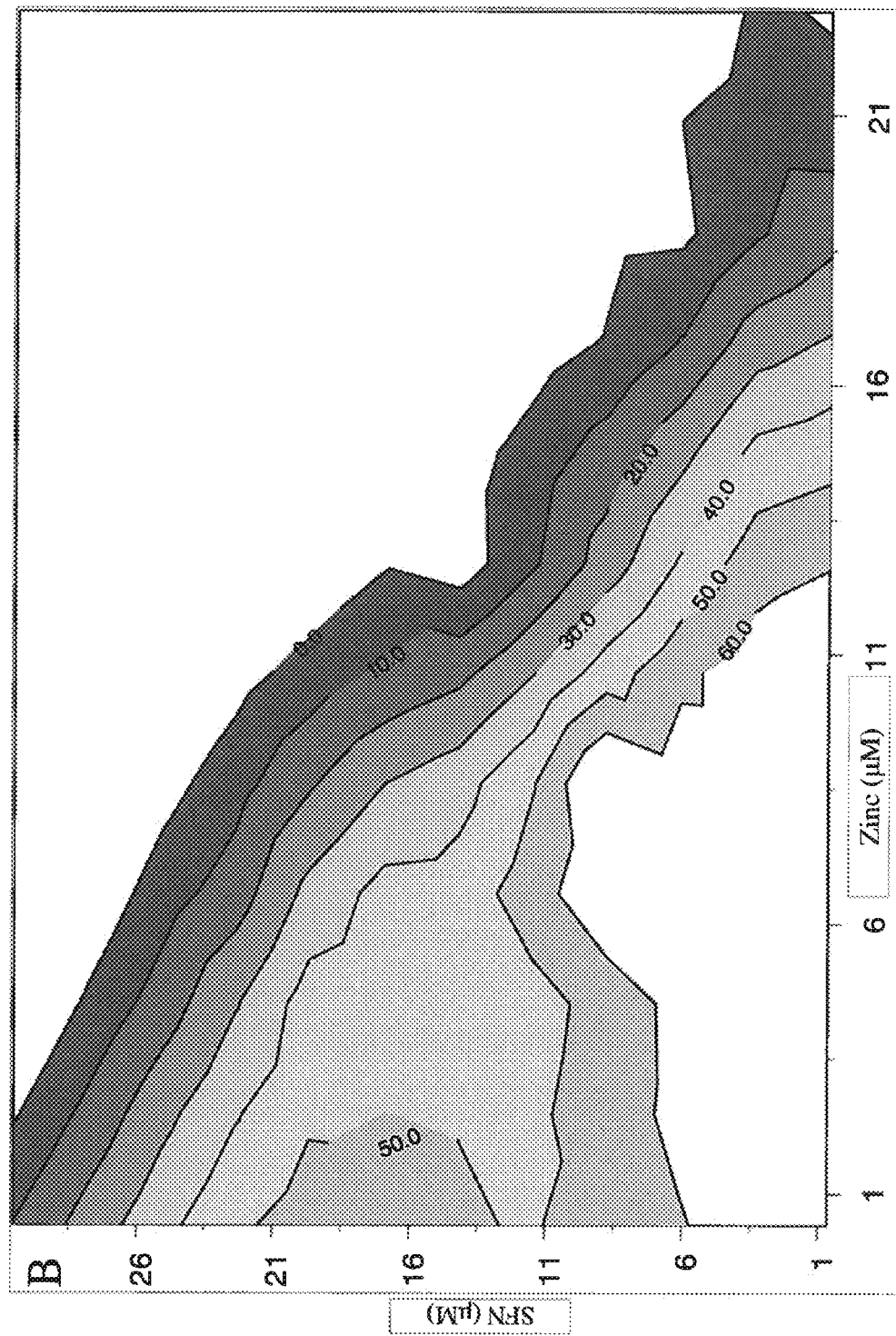
Fig. 2. Determination of combinational effect of zinc and SFN on PC-3 cells

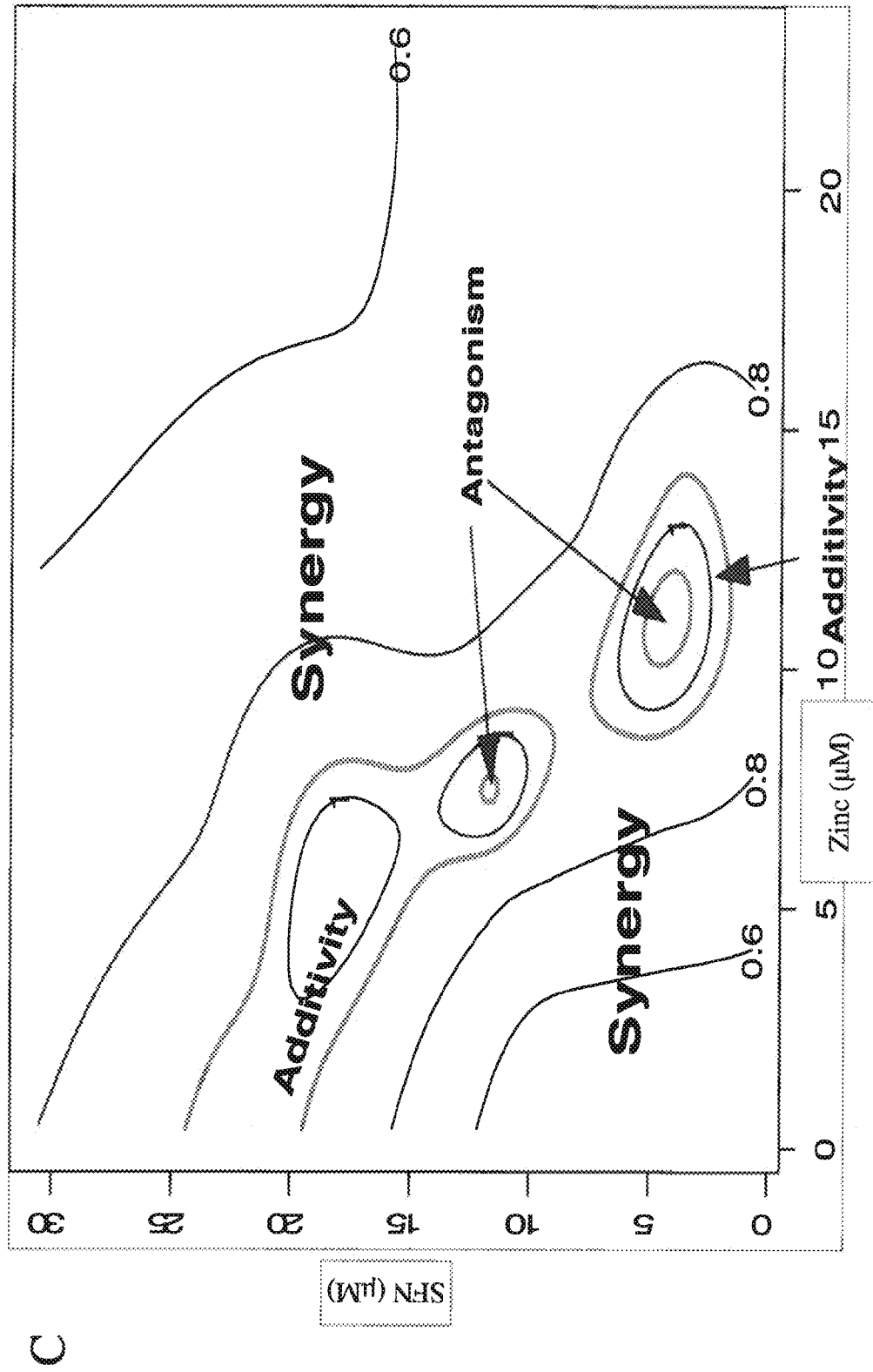

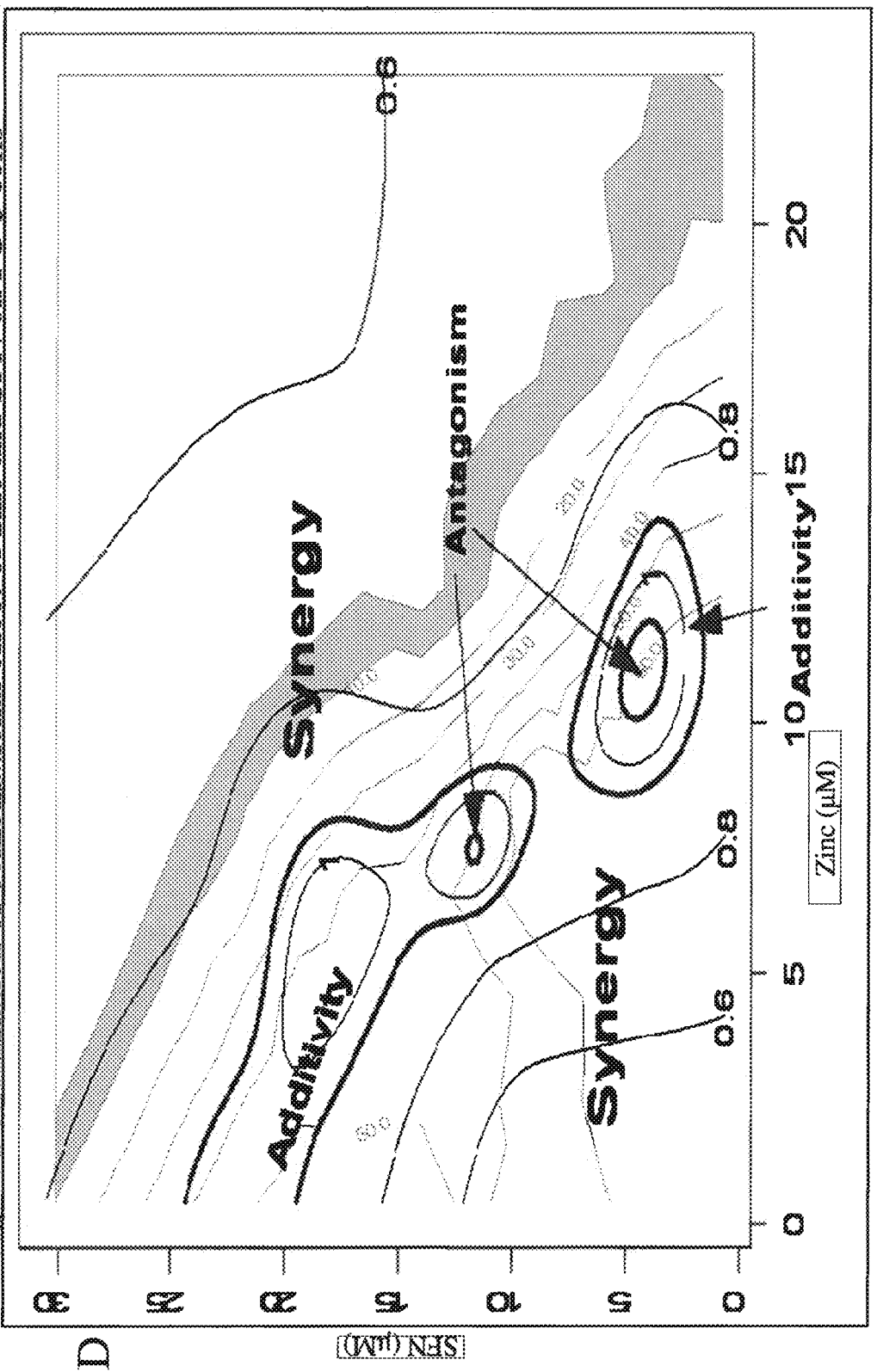

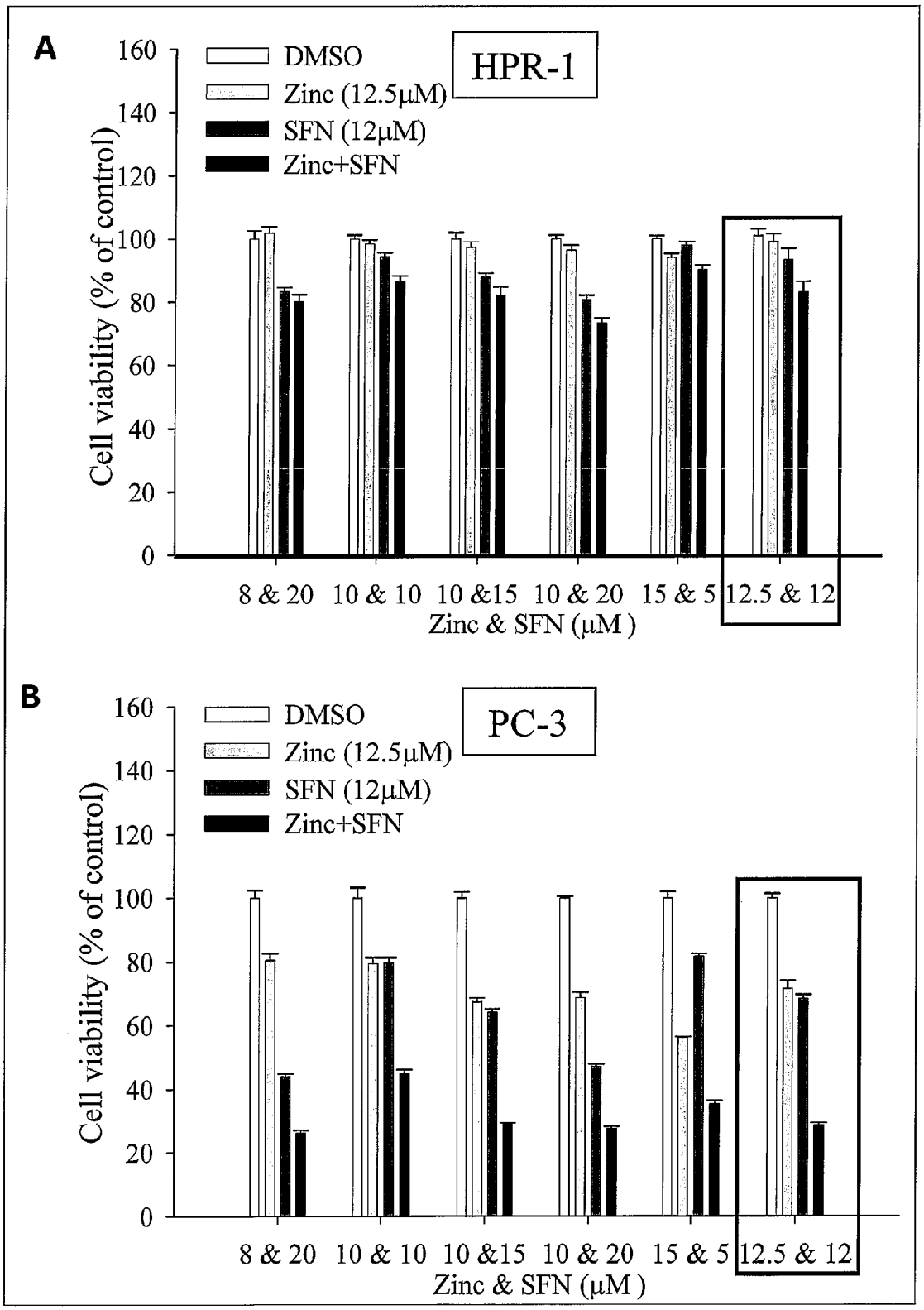
Fig.3 Effect of the combinations of zinc and SFN on viability of HHPR-1 and PC-3 cells

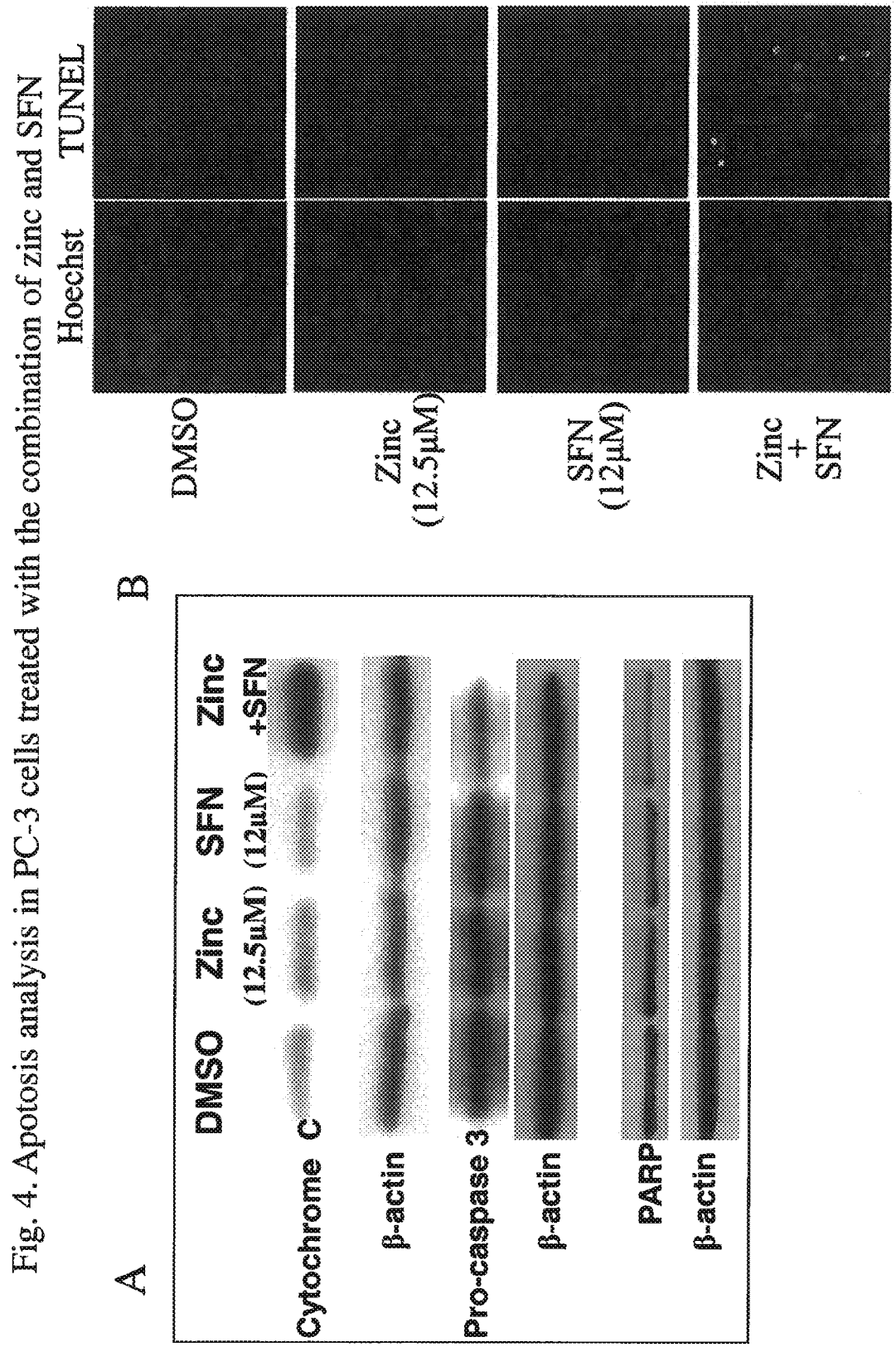
Fig. 4. Apotosis analysis in PC-3 cells treated with the combination of zinc and SFN

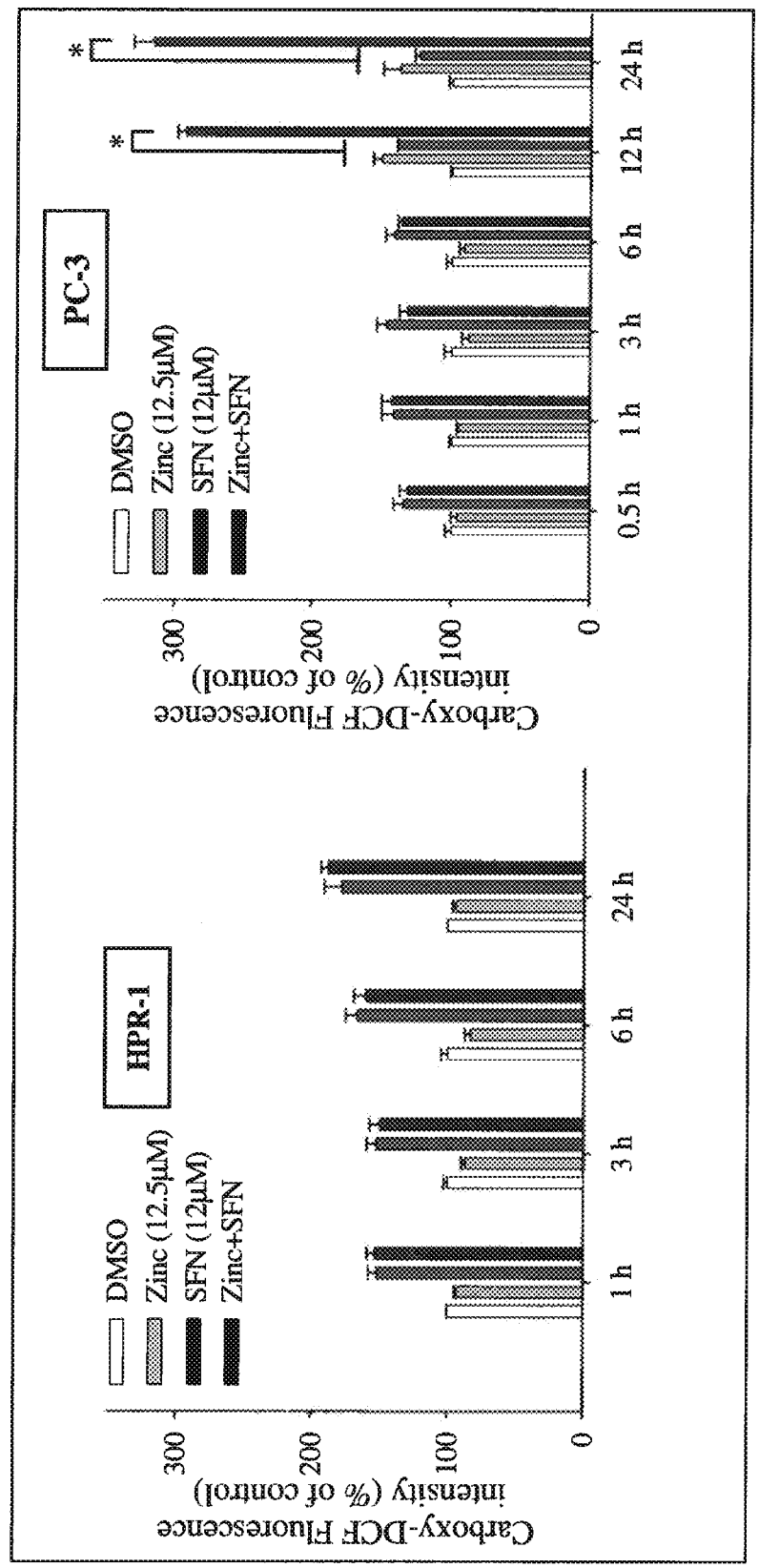
Fig. 5. ROS generation in PC-3 cells treated with the combination of zinc and SFN

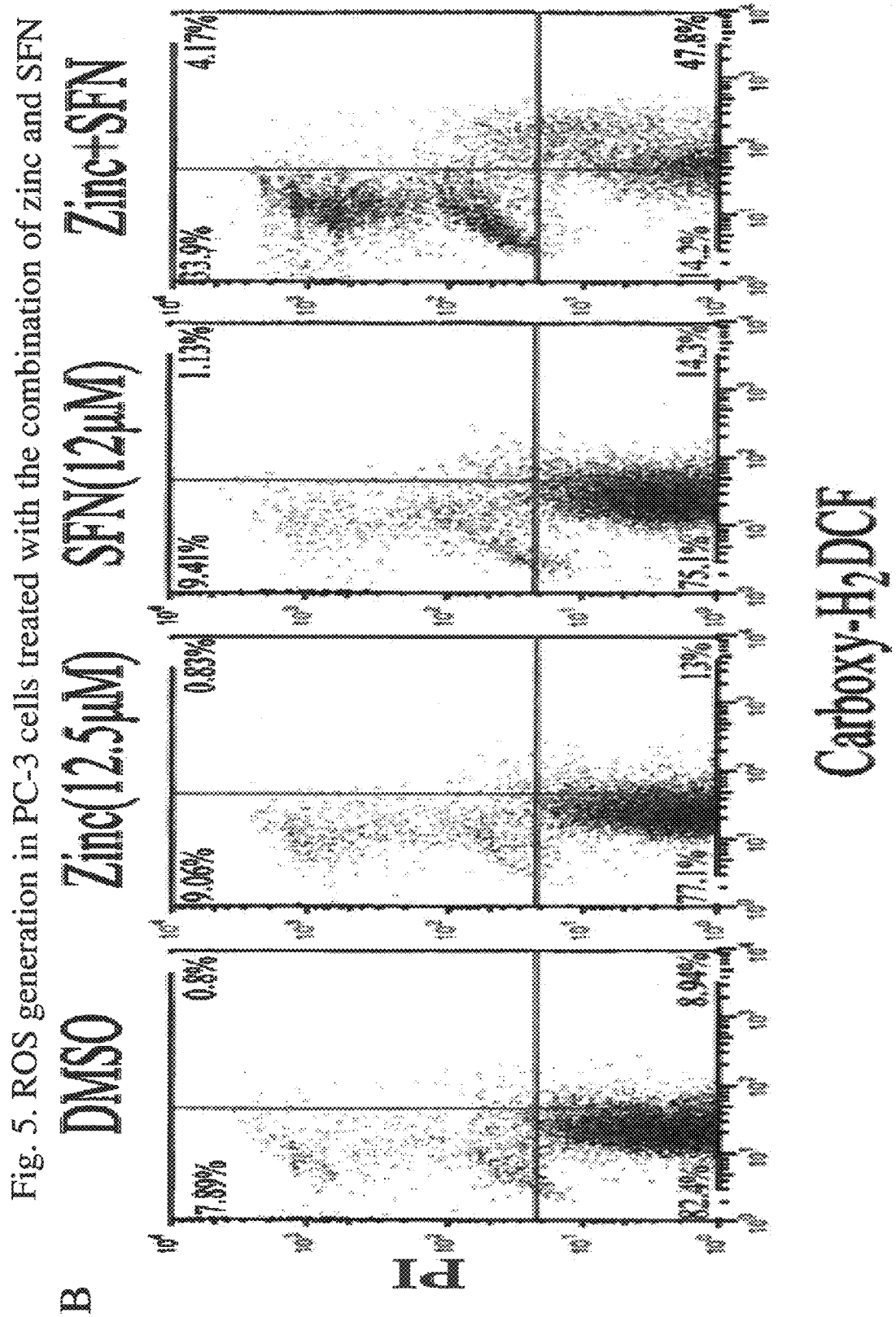

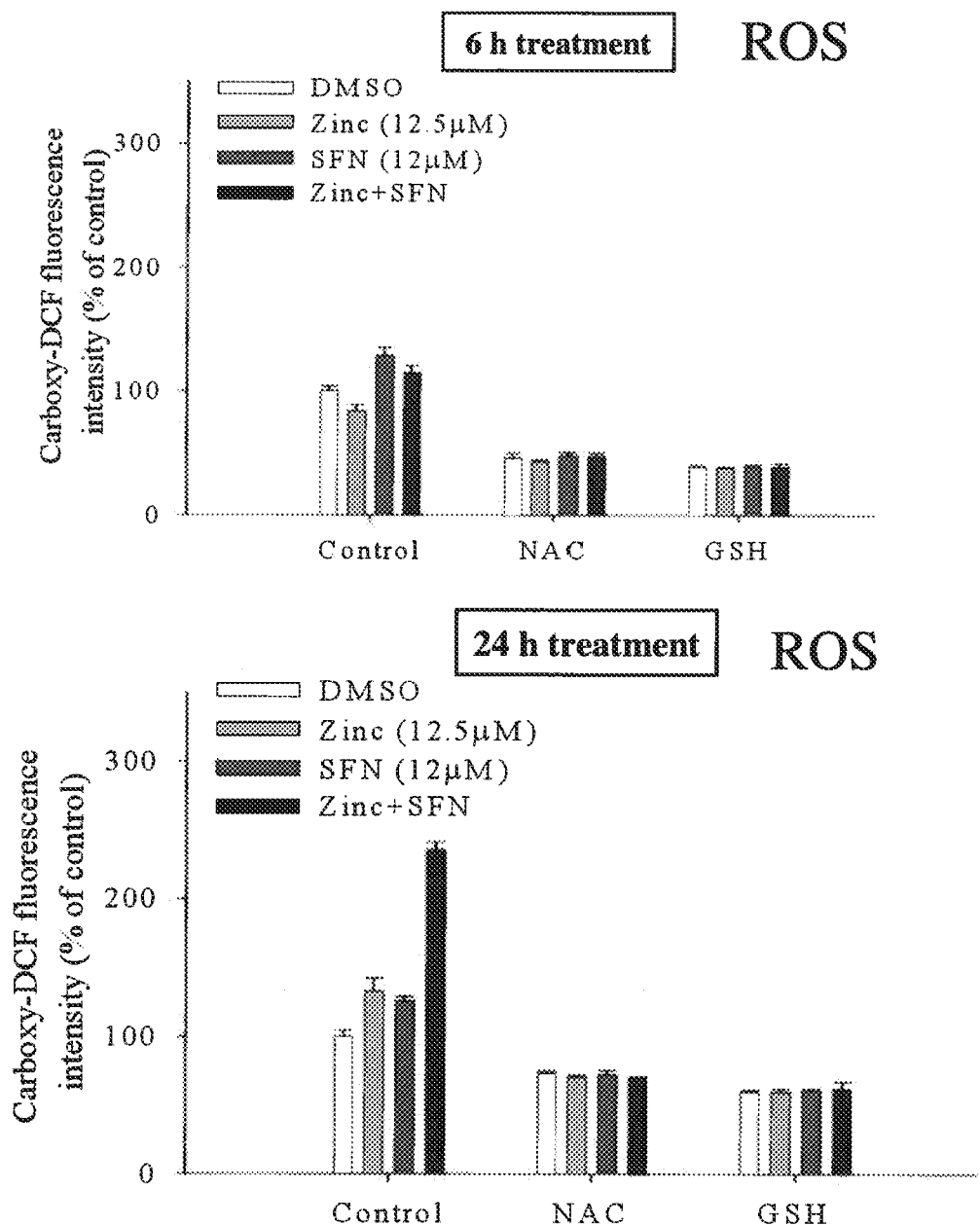
Fig. 5. ROS generation in PC-3 cells treated with the combination of zinc and SFN

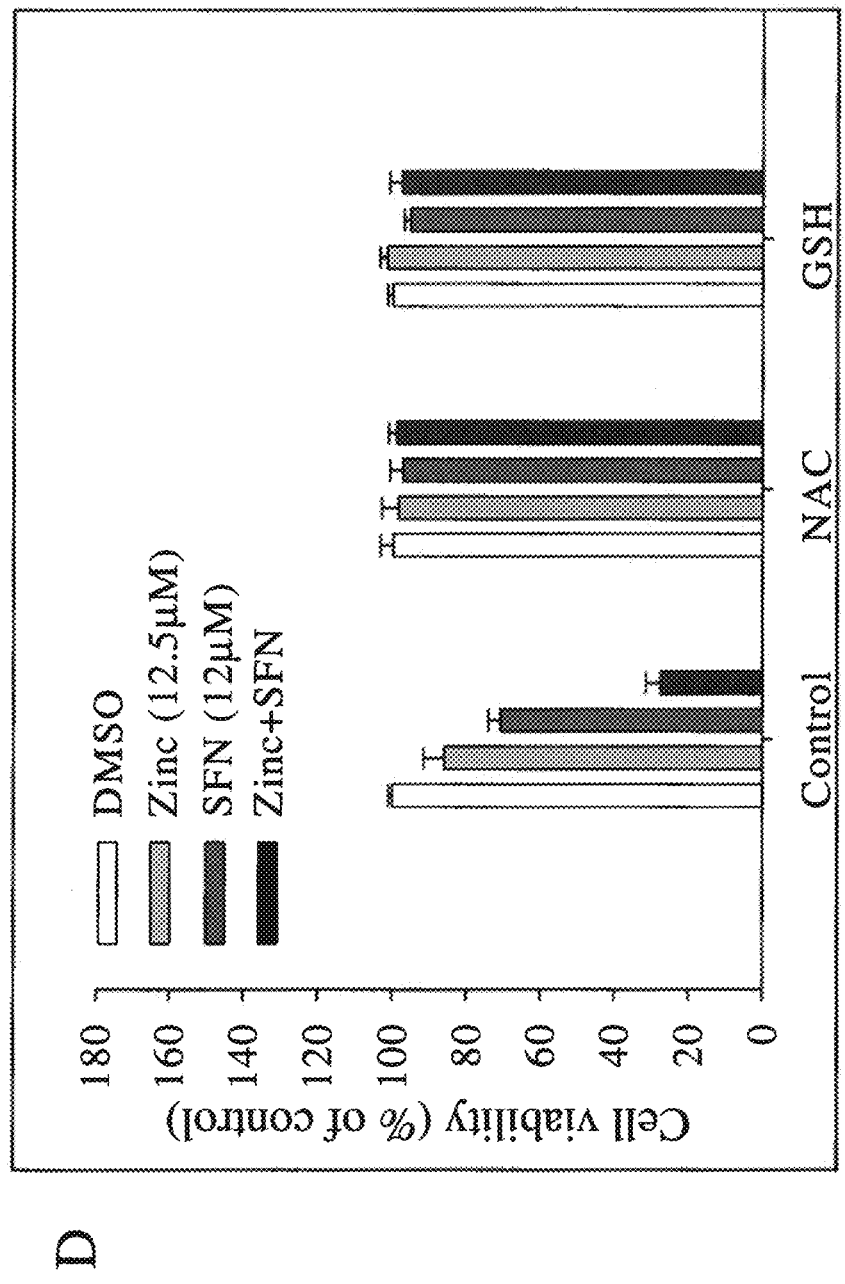
Fig. 5. ROS generation in PC-3 cells treated with the combination of zinc and SFN

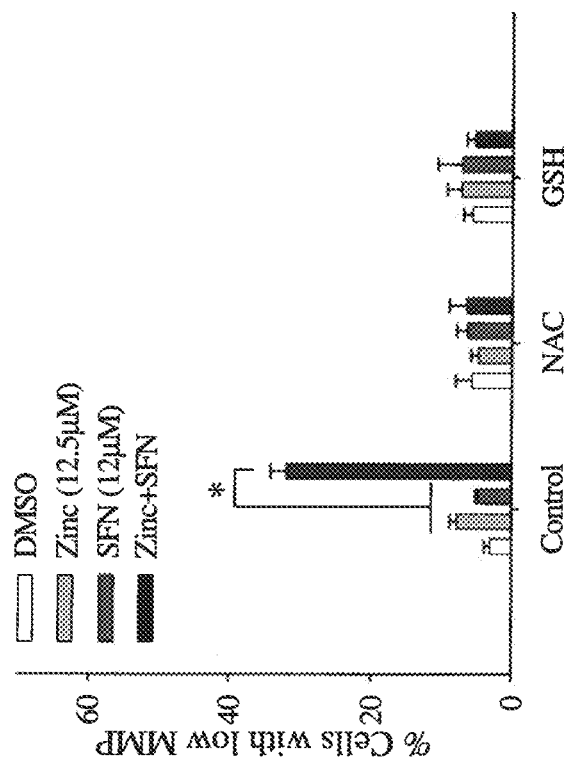
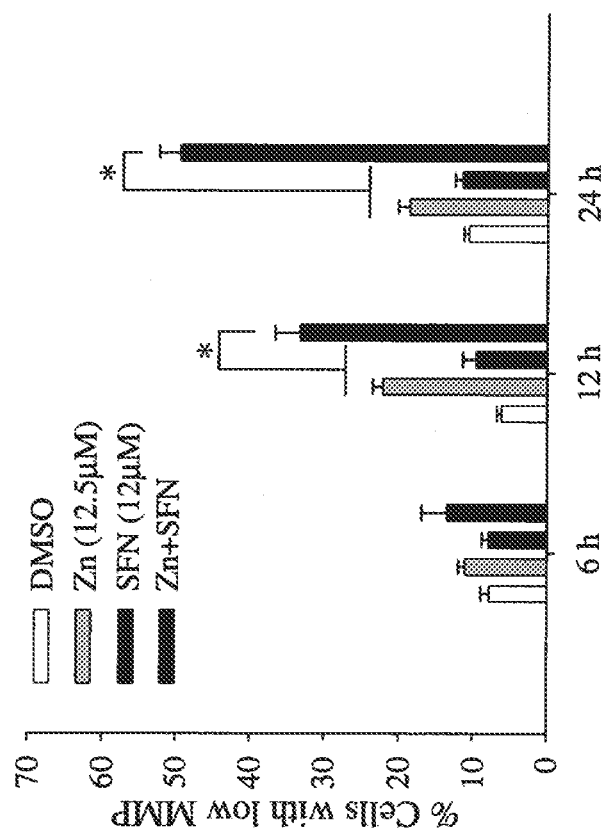
Fig. 6. Mitochondria membrane potential determination in PC-3 cells treated with the combination of zinc and SFN

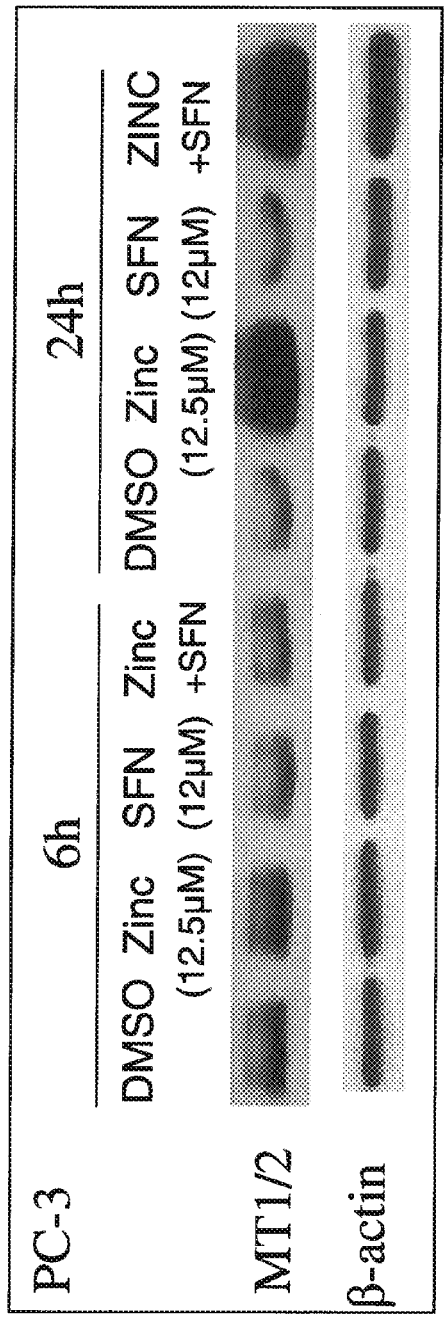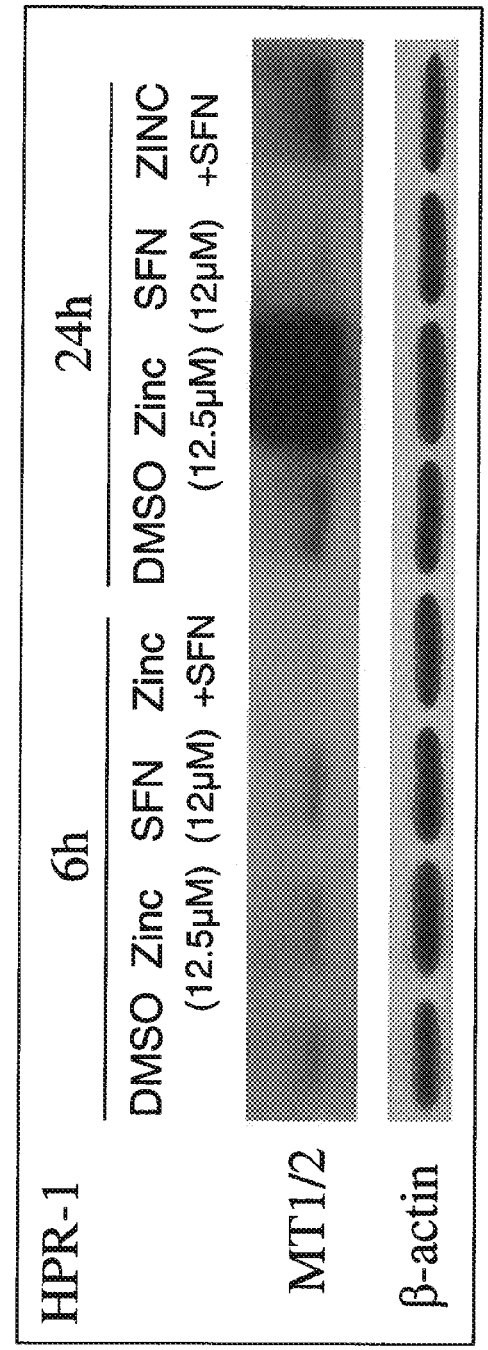
Fig. 7. MT1/2 expression with the combination of zinc and SFN

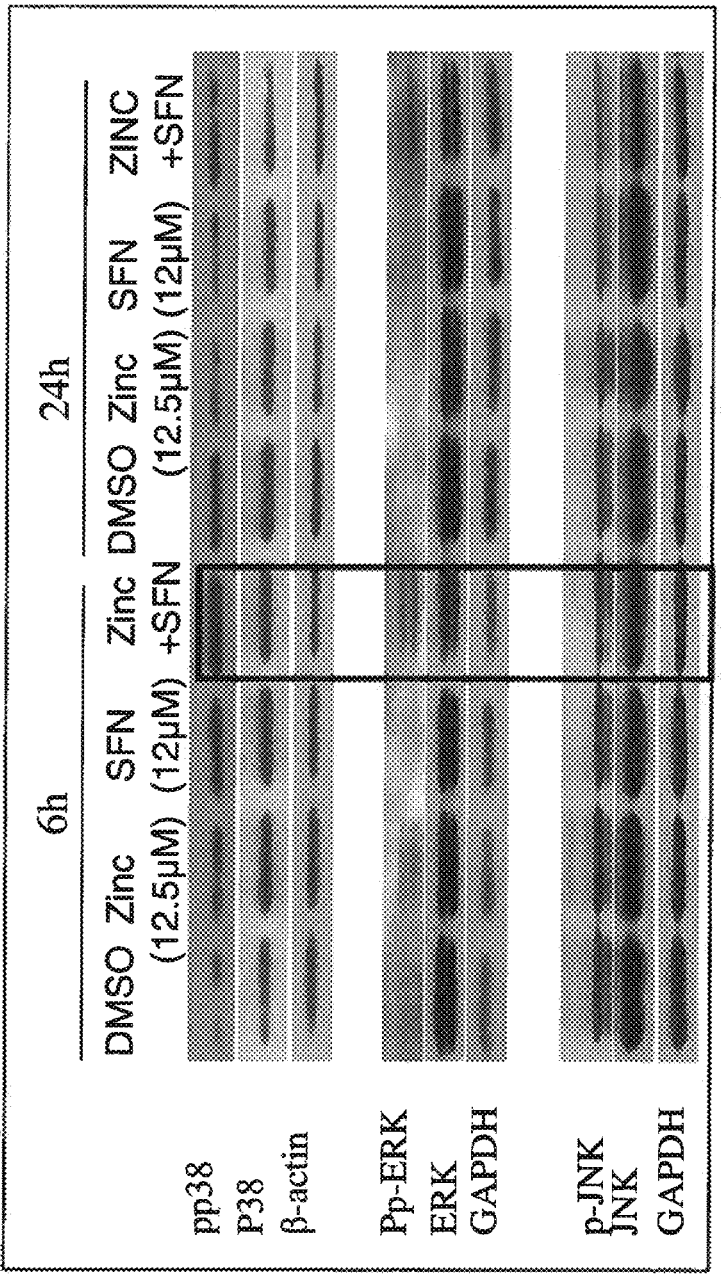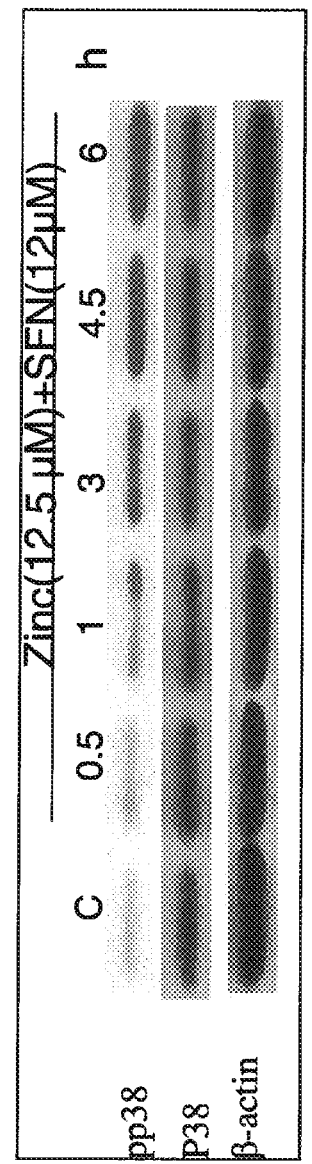
Fig. 8. MAPKs activation with the combination of zinc and SFN

POTENT INHIBITORY EFFECT OF ZINC IN COMBINATION WITH SULFORAPHANE ON CANCER CELL GROWTH

CROSS-REFERENCE TO RELATED APPLICATIONS

This application claims the benefit of U.S. Provisional Patent Application Ser. No. 61/146,342, filed Jan. 22, 2009 which is incorporated by reference herein in its entirety.

STATEMENT OF GOVERNMENTAL INTEREST

This invention was made with government support under Grant Number CA 116815 awarded by the National Institutes of Health. The government has certain rights in the invention

BACKGROUND OF THE INVENTION

1. Field of the Invention

The invention generally relates to cancer treatment. In particular, the present invention relates to methods for preventing or treating tumor growth, including prostate cancer, using a composition comprising a combination of zinc and sulforaphane (SFN).

2. Description of the Related Art

Prostate cancer is the sixth mostly frequently diagnosed cancer in the world, the most common cancer and the second leading cause of death due to cancer in men in the United States [1,2]. In addition, prostate cancer accounts for 29% (218,890) of new cases in man and becomes the biggest killer of men over 85 years in the United States [3,4]. Conventional therapies against prostate cancer include radiation therapy and radical prostatectomy, while more than one third of these cases will develop metastases which are further targeted by androgen ablation therapy [5]. However, some of the metastases turn androgen-independent, which renders androgen ablation therapy less effective. Therefore, more research on advanced therapies is needed to obtain better anti-cancer treatments for therapeutic/clinical purposes.

Zinc, as a form of daily diet, is an essential element for functionality of about 300 enzymes, DNA stabilization and gene expression [6]. Besides, it has been estimated that up to ten percent of all mammalian proteins bind zinc for their structure maintenance and normal activities [7]. A recent study has proposed that Zinc can serve as a signaling molecule which transfers signals in two distinct stages: 1) in early signaling, released zinc from endoplasmic reticulum (ER), as a second messenger, transfers extracellular stimulus inside cells in a calcium and mitogen-activated protein kinase (MAPK) dependent manner; 2) in late signaling, zinc may induce different expression profile [8]. The so-called late zinc signaling has been confirmed in our recent studies.

It has been well established that normal human prostate gland contains the highest zinc level among the whole body. When prostate cells become malignant, there is a dramatic decrease of cellular zinc (60-70% loss) [9]. Although the specific mechanism of such decreased zinc level in prostate cancer cells is not fully understood, our previous findings indicated that decreased expression of zinc-binding protein metallothioneins (MTs) in prostate cancer may contribute to such loss of zinc levels [10]. Furthermore, we also observed that high zinc levels could be restored in the androgen-independent malignant prostate cell line, PC-3, after zinc supplementation in vitro. It is observed that zinc exposure also induces apoptosis in PC-3 cells via mitochondria-dependent pathway, in contrast zinc-induced cell apoptosis was not observed in normal prostate cell line HPR-1 cells [11-13].

Besides trace elements like zinc, many diet foods have also been largely studied for their potential effect against cancer in recent years. Epidemiologic studies continues to support that dietary intake of cruciferous vegetables (such as broccoli and cabbage) can reduce cancer risk at sites including prostate [14-16]. Accordingly, compounds hided inside these vegetables become of interest. Among those responsible for such anticancinogenic effect of these vegetables, organic isothiocyanates (ITCs) have been considered to play a major role. SFN (1-Isothiocyanato-4-methylsulfinylbutane), as a member of ITCs family, is found highly in broccoli and broccoli sprouts [17]. Generation of SFN is conducted via hydrolysis of glucosinolates by myrosinase released when these vegetables are chewed. Since its isolation, growing studies has been focused on it due to its anticarcinogenic action as a nature product from diet. Multiple mechanisms such as inhibition of phase 1 and 2 enzymes are thought to explain its effect on cancers [18]. Due to these anticarcinogenic actions of SFN, it has been used to combine with other traditional chemotherapeutic agents to generate synergistic tumor inhibitory effect. Tumor necrosis factor-related apoptosis inducing ligand (TRAIL), for example, was used together with SFN to boost its effect against lung and liver cancers [19,20]. Therefore, SFN might be a good candidate in terms of combinational application with other anticarcinogenic regents. However, whether SFN can sensitize prostate cancer cells to zinc effect has previously not been studied or evaluated. Thus, there is a need to identify and validate combinations of SFN and other therapies which can have therapeutic applications for treating various cancers.

BRIEF SUMMARY OF THE INVENTION

This invention is directed to pharmaceutical compositions comprising zinc and sulforaphane and to methods for treating or preventing cancer using those compositions. The modulation of MAPK pathway proteins and metallothionein is implicated in the inhibitory effect observed with these compositions.

Specific examples of cancers that can be treated by this method include, but are not limited to: cancer of the head, neck, eye, mouth, throat, esophagus, chest, bone, lung, colon, stomach, breast, ovaries, kidney, liver, brain, bladder, uterus, pancreas, and prostate.

In one embodiment of the invention, the invention encompasses a method of treating prostate cancer in a patient comprising administering SFN and zinc wherein the amount of SFN administered to the patient can range from milligram to gram levels and the amount of zinc administered can range from about 15 to 100 mg/day. Oral administration is a typical route of administration.

In another embodiment, the invention encompasses a method of treating cancer in a patient comprising administering SFN and zinc wherein the combination treatment yields a synergistic growth inhibitory effect on the patient cancer cells.

In another embodiment, the invention encompasses a method of treating cancer in a patient comprising administering SFN and zinc wherein the combination treatment increases apoptosis in the cancer cells.

In another embodiment, the invention encompasses a method of increasing the therapeutic efficacy of SFN for treating cancer comprising administering to a patient in need thereof an amount of zinc that is sufficient to increase the therapeutic efficacy of the SFN.

In another embodiment, the invention encompasses a kit for used in the treatment or prevention of cancer which comprises a therapeutically effective amount of SFN and a therapeutically effective amount of zinc.

BRIEF DESCRIPTION OF THE DRAWINGS

FIG. 1. Differential responses to zinc and SFN on cell viability in HPR-1 and PC-3 cells. HPR-1 and PC-3 cells were treated with zinc (A) and SFN (B), respectively, at different concentrations as indicated for 24 h, and the viable cell numbers were determined by MTT assays. The cell viability was calculated by the equation: (OD value of sample−OD value of MTT solution)/(OD value of control−OD value of MTT solution). The results are expressed by Mean±SE and each experiment was repeated at least 3 times.

FIG. 2. Statistical analysis for determining the dosages of the combinations of zinc and SFN to study their inhibitory effect on PC-3 cell growth. Based on the MTT assay data presented at Table 1, the computerized statistical analyses were conducted and presented in: (A) The cell growth response surface was generated according to the cells' response to a series of combinations of zinc and SFN; (B) The contour plot was transformed from the response surface; (C) A contour plot of interaction index surface was generated by SynStat version 1.beta software. The red lines indicate the area containing 95% confidence surface for additive action (the interaction index=1). The synergistic effect of combined zinc and SFN is marked with lines. (D) View of overlapping B and C to provide the high probability for selection of drug dosages used in combinations with potent synergistic inhibitory effect.

FIG. 3. Growth inhibitory effect of selected combinations of zinc and SFN on HPR-1 and PC-3 cells. HPR-1 (A) and PC-3 (B) cells were treated for 24 h with or without zinc, SFN and their combinations, respectively as indicated. The cell viability was determined by MTT assay and the results were calculated using the same method as described in FIG. 1. A boxed field indicates the combination of zinc and SFN that was selected in following experiments.

FIG. 4. Characterization of apoptosis in PC-3 cells treated with the combination of zinc and SFN. PC-3 cells were treated with or without zinc (12.5 µM), SFN (12 µM) and their combination, respectively, for 24 h. (A) The effects of the treatments on the cellular levels of cytochrome c, pro-caspase 3 and PARP were studied by Western Blot analyses using specific antibodies as indicated. (B) Apoptotic effect of the combination of zinc and SFN was identified by TUNEL assay. After treatment, the cells were stained with TUNEL kit according to the manufacturer's instruction and Hoechst 33258 was used for nuclei staining to localize the cells. The results were photographed with a fluorescence microscope (Nikon eclipse E8000). The experiments were repeated at least 3 times.

FIG. 5. Differential ROS production and cell viability in PC-3 and HPR-1 cells induced by the combination of zinc and SFN. (A) Time-course study of ROS production in PC-3 and HPR-1 Cells treated with or without zinc, SFN or their combination, respectively, at the concentrations as indicated for 0.5, 1, 3, 6, 12 and 24 h (PC-3 cells) and for 1,3, 6 and 24 h (HPR-1 cells). (B) Induction of ROS production was identified in live PC-3 cells. After 24 h treatment, cells were stained with carboxy-DCFDA and PI, and the cell flow cytometry data showed the relationship of cell viability and ROS production. (C) Inhibition effect of NAC (6 mM) and GSH(6 mM) on ROS production induced by the combination of zinc and SFN in PC-3 cells. PC-3 cells were pretreated with NAC or GSH for 30 min, and then the treatments were added as indicated for 6 h and 24 h, respectively. ROS production was detected using the same method described in (A). (D) NAC and GSH abolished growth inhibitory effect of zinc and SFN in PC-3 cells. The cells were treated as the same as in C and the cell viability was determined by MTT assay. Statistical analysis for comparison of effect of zinc, SFN and their combination was performed with Student's t-Test.*represents p<0.05. All experiments were repeated at least 3 times.

FIG. 6. Alternation of mitochondrial membrane potential (MMP) in PC-3 cells treated with the combination of zinc and SFN. (A) Time-course study of the induction of MMP changes in PC-3 cells with the treatments as indicated for 6, 12 and 24 h, respectively. (B) Inhibitory effect of NAC and GSH on MMP alterations induced by the combination of zinc and SFN. PC-3 cells were pretreated with NAC or GSH for 30 min, followed by the treatments as indicated for 24 h. MMP was detected by Dioc6 (3) and PI staining according to the company's instruction and cell flow cytometry analysis. The number of the cells with loss of MMP is displayed as a fraction (0-100%) of total number of cells. Statistical analysis was performed as described in FIG. 5. * represents p<0.05 All experiments were repeated at least 3 times.

FIG. 7. Differential inhibitory effect of the combination of zinc and SFN on MT1/2 expression in PC-3 and HPR-1 cells, respectively. Western Blot analysis of MT1/2 expression was conducted in PC-3 cells (A) and HPR-1 cells (B). Total cellular protein was extracted from treated cells as indicated and applied for the immunoblots using antibodies against MT1/2 and 3-actin. The latter was used as the internal controls. The experiments were repeated 3 times and the representative blots are shown.

FIG. 8. Detection of MAPKs activation induced by the combination of zinc and SFN in PC-3 cells. (A) Western Blot analysis of p38, ERK and JNK activation. The cells were treated respectively as indicated for 6 and 24 h. Total cellular protein was extracted and applied to immunoblots using specific antibodies as indicated and β-actin and GAPDH were used as the internal controls. A boxed field indicates the significant activation of the kinases' activities including p38 and ERK. (B) A time-course study of p38 activation in PC-3 cells treated with the combination of zinc and SFN.

DETAILED DESCRIPTION OF THE INVENTION

Definitions

As used herein, the term "cancer" includes but is not limited to solid tumors and blood born tumors. The term cancer refers to disease of skin tissues, organs, bone, cartilage, blood and vessels. The invention encompasses the treatment of various types of cancer including but not limited to cancer of the head, neck, eye, mouth, throat, esophagus, chest, bone, lung, colon, rectum, stomach, breast, ovaries, kidney, liver, brain, prostate, and pancreas. The term "cancer" further encompasses primary and metastatic cancers, unless otherwise indicated.

As used herein to describe a compound or chemical moiety, the term "derivative" means a compounds or chemical moiety wherein the degree of saturation of at least one bond has been changed (e.g., a single bond has been changed to a double or triple bound) or wherein at least one hydrogen atom is replaced with a different chemical moiety. Examples of different atoms and chemical moieties include but are not limited to, halogen, oxygen, nitrogen, sulfur, hydroxy, methoxy, alkyl, amine, amide, ketone, and aldehyde.

As used herein, the term "prodrug" means a derivative of a compound that can hydrolyze, oxidize, or otherwise react under biological conditions (in vitro or in vivo) to provide the compound.

Apoptosis is a form of programmed cell death in multicellular organisms. It is one of the main types of programmed cell death which involves a series of biochemical events leading to a characteristic cell morphology and death, including blebbing, changes to the cell membrane such as loss of membrane asymmetry and attachment, cell shrinkage, nuclear fragmentation, chromatin condensation, and chromosomal DNA fragmentation. Processes of disposal of cellular debris whose results do not damage the organisms differentiate apoptosis from necrosis.

Synergistic effect is a biological response to exposure to multiple chemicals (agents) which is greater than the sum of the effects of the individual agents. It is an effect that occurs when two or more agents (for example medications) have a more powerful effect when used together than either has been used alone. Many chemotherapeutic agents have synergistic effects, and chemotherapy regimens often include treatment with more than one drug.

This invention is based in part on the finding that SFN can effectively enhance the apoptotic effect of zinc on prostate cancer cells in a synergistic fashion. Embodiments of the invention include a method of treating or preventing cancer which comprises the administration of SFN or a derivative or analog thereof in combination with zinc to a patient. The synergistic effect of these two compounds on tumor cells results in high efficiency and decreased toxicity by reducing the treating dosage for each compound. Possible mechanisms for such combinatorial effect are thought to include (1) attenuation of zinc effect on MT1/2 proteins by SFN; (2) synergistic effect of zinc and SFN on ROS generation; (3) synergistic activation of P38 by zinc and SFN. Clearly, there may be other possible operative mechanisms which explain the observed effect. These data help to explore the possibility of reducing dosage of each reagent while maintaining a major inhibitory effect on prostate cancer cells and to provide a better methodology for cancer treatment. In short, the invention encompasses the therapeutic effects that result from the unexpected and unique synergy between SFN and zinc on cancer cells.

Human Prostate Cell Lines and Zinc Treatment

Two human prostatic cell lines were used: a) HPR-1, a cell line derived from normal human prostate epithelial cells (kindly provided by Dr. C. K. Choo, University of Hong Kong, Hong Kong, China); and b) PC-3, a human malignant prostate cell line (ATCC, Rockville, Md.). HPR-1 cells were cultured in keratinocyte medium supplemented with epidermal growth factor (EGF) (2.5 mg/500 ml) and bovine pituitary extracts (25 mg/500 ml) (Gibco BRL, Life Technologies, Bethesda, Md.). PC-3 cells were cultured in RPMI-1640 medium with 5% or 10% of fetal bovine serum (FBS), respectively. All media were supplemented with penicillin/streptomycin (1 U/ml, Invitrogen), and the cells were maintained at 37° C. in a humidified incubator with 5% $CO_2$. The passages of the cell lines were within the range of 5-40. Once the cell density reached 50-60% confluence, the growth media were replaced by fresh serum/supplement-free medium for 24 h to synchronize cell growth. The cells were then treated with or without zinc sulfate (concentrations as indicated in the legends) in fresh serum/supplement-free medium for 0, 1, 3, 6, 12, and 24 h, respectively.

3-(4,5-dimethylthiazol-2-yl)-2,5-diphenyltetrazolium bromide (MTT) assay

Cell viability and proliferation were evaluated with the MTT assay. The cells were seeded at a density of 9× $10^3$ cells/well in a 96 well plate containing 100 µl culture medium/well. After attachment, cells were treated with or without zinc and/or SFN at various concentrations in serum/supplement free medium. After 24 h treatment, 10 µl MTT (5 mg/ml, sigma) was added into each well and incubated at 37° C. for 1 h. Then the medium was removed and 100 µl dimethyl sulfoxide (DMSO) was added to dissolve water-insoluble formazan crystals converted from water-soluble MTT by living cells. The color absorbency of formazan was detected at a wavelength of 540 nm using a microplate reader (Molecular Devices).

Western Blot Analyses

Total cellular proteins from the experimental samples were extracted by radioimmuno-precipitation assay (RIPA) lysis buffer (Upstate, Lake Placid, N.Y.) containing protease inhibitor (Roche Diagnostics Gmbh, Mannheim, Germany). The protein extracts (30 µg/lane) were applied to electrophoresis on an SDS-polyacrylamide gel, and then, a transferred poly(vinylidene fluoride) (PVDF) membrane (Millipore, Billerica, Mass.) was blocked in 5% nonfat dry milk in phosphate buffered saline (PBS) containing 0.05% Tween-20 (Sigma, St. Louis, Mo.) (PBST) for 1 hr at room temperature followed by the hybridization to the primary antibodies against PARP (BD pharmingen, San Jose, Calif.), caspase 3 (BD pharmingen, San Jose, Calif.), p-JNK and JNK1 (Santa Cruz, Calif.), pP38 and P38 (Cell Signaling Technology, Danvers, Mass.), ppERK1/2 (Sigma, St. Louis, Mo.), ERK1/2 (Cell Signaling Technology, Danvers, Mass.) at 4° C. overnight. After washing, the membranes were incubated with corresponding second antibodies. Beta-actin (Sigma, St. Louis, Mo.) and GAPDH (Cell Signaling Technology, Danvers, Mass.) were used as internal controls to monitor the sample loadings. The specific binding signals were visualized by enhanced chemiluminescence (ECL) (Pierce, Rockford, Ill.) according to the manufacturer's instructions. The signals of targeted bands were scanned and quantified with an LKB Ultra Scan XL laser densitometer (Image Quant, Molecular Dynamics, Sunnyvale, Calif.).

For cytochrome C detection, cells were fractionated as previously reported [1]. Briefly, cells were collected and washed once with PBS. Then cells were homogenized on ice with a Dounce homogenizer (80 strokes) in extraction buffer containing 250 mM sucrose, 20 mM HEPES (PH 7.2), 1.5 mM $MgCl_2$, 1 mM EDTA, 10 mM KCl, 1 mM EGTA, and protease inhibitors tablet (1 tablet/10 ml). The homogenates were centrifuged twice at 750 g for 5 min at 4° C., to remove nuclei and debris. The supernatants were further centrifuged at 10,000 g for 30 min. The supernatants were removed and stored at −80° C. until analysis by SDS-polyacrylamide gel electrophoresis. The primary antibody for cytochrome C was purchased from BD Biosciences Pharmingen (San Jose, Calif.).

Statistical Methods for Combination Study

To study combinations of SFN with zinc in PC-3 cell lines, the combination $$\frac{x_A}{X_A} + \frac{x_B}{X_B} = \tau$$

experiments were designed by a statistics-based method utilizing the maximal power design developed by Fang and Tan(2003, 2008) and the corresponding SynStat version 1.beta software (http://www.umgcc.org/research/biostat_software.htm), This method uses uniform measures maximizes the minimum power of the F-test to detect departures from the additive action of drugs. It does not assume a constant relative potency of the two drugs. With the information from experiments of single agents, SynStat derived 21 mixtures of the two agents and 6 replicates at each mixture based on the pooled variations in single agent experiments, which have 80% statistical power to detect at least a 15% difference in viability between the predicted additive values and the observed values at a significance level of 5%. Then, cells are exposed to these 21 mixtures and the cytotoxicity of this combination is determined. Upon completion of the experiments, we use the F-statistic given by Tan et al. (2003) to test the hypothesis of the additive action of two agents and calculate the p-value of the F-test. If the p-value is greater than 0.05, we can accept the hypothesis of the additive action of two agents. Otherwise, we calculate the interaction index ($\tau$), which is proposed by Berenbaum who adopted the Lowe additivity model (Berenbaum, 1977) where, for a given cytotoxic effect, $x_A$ and $x_B$ are the concentrations of zinc and SFN in the combination, and $X_A$ and $X_B$ are the concentrations of zinc and SFN respectively that achieve the same cytotoxic effect when given alone. A $\tau$ value of 1 indicates additivity; $\tau<1$ indicates synergy, and $\tau>1$ indicates antagonism. Then the combination index surface can be fitted using two dimensional B-spline (Thin plate spline) method (Fang et al. 2008) and the corresponding contour plot shows the dose-mixture areas of the additive action, synergism and antagonism for the joint action of two agents Mitochondrial Membrane Potential (MMP) Detection Cell flow cytometric analysis with 3,3'-dihexyloxacarbocyanine iodide (DiOC6(3); Invitrogen, Carlsbad, Calif.) and propidium iodide (PI;BD Pharmingen, San Jose, Calif.) was used to evaluate MMP and apoptosis of the cells. The fluorescence dye DiOC6(3) is featured by its accumulation in the mitochondrial matrix, which is resulted from negative mitochondrial membrane potential within viable cells. Thus, the changes of fluorescence of DiOC6(3) reflect the MMP alteration of the cells. Another fluorescence dye PI is cell membrane impermeable and able to stain DNA once cell membrane integrity is damaged during apoptosis. In the experiments, after treatments, cells ($2.5\times10^5$/ml) were incubated with 100 nM DiOC6(3) in PBS for 15 min at 37° C. Then the cells were washed in PBS once, followed by incubation with 2.5 µg/ml PI for additional 10 min at room temperature. The samples were subjected to cell flow cytometric analysis, and FACScan (Becton Dickinson) was used to analyze the fluorescence of DIOC6(3) and PI [2].

ROS Detection 5-(and-6)-carboxy-2',7'-dichlorodihydrofluorescein diacetate (carboxy-$H_2$DCFDA,) was used to determine the intracellular ROS levels of individual cells. In living cells, this compound is oxidized and converted to the 2',7'-dichlorofluoroscein (DCF) that is highly fluorescent. In the experiments, PC-3 cells cultured on 12-well plates were incubated in serum-free medium containing zinc sulfate (12.5 mM)/SFN (12 µM). Thirty min prior to the completion of the time course, carboxy-H2DCFDA was added at a final concentration of 5 µM. Cells were then collected and washed once with PBS. The fluorescent intensity of DCF was assayed by FACScan (Becton Dickinson)[3].

TUNEL Assay

Terminal deoxynucleotidyl transferase dUTP nick end labeling (TUNEL) assay was carried out using an in situ cell death detection kit (Roche, Indianapolis, Ind.). PC-3 cells were grown on the cover slips placed in a 12-well plate. After attachment, cells were treated with serum free medium containing zinc (12.5 µM) and/or SFN (12 µM). After 24 h treatment, the cells were fixed with 4% paraformaldehyde (USB, Cleveland, Ohio) for 1 h at room temperature and permeabilized with 0.1% sodium citrate containing 0.1% Triton X-100 (Sigma, St. Louis, Mo.) on ice for 2 min. Cells were then incubated with 50 µl of TUNEL reaction mixture in the dark in a humidified chamber at 37° C. for 1 h. After cells were washed three times with PBS, cells were then incubated with Hoechst 33258 (0.1µg/ml, Molecular Probes, Eugene, Oreg.) for 10 min at 37° C. and then washed three times with PBS. Finally, the cells were mounted to the slides with aqueous antifade medium (Polyscience, Warrington, Pa. The apoptotic cells were determined and photographed using a fluorescence microscope (Nikon Eclipse E800).

Differential Cell Viability of Normal and Malignant Human Prostate Cells in Responses to Zinc and SFN Treatment To ascertain whether the growth effect of zinc and SFN exhibits with the cell-type specific property the dose response experiments with zinc and SFN were independently carried out in normal prostate epithelium cell line HPR-1 and prostate malignant cell line PC-3 cells (FIG. 1). The cells were incubated with zinc (FIG. 1A) or SFN (FIG. 1B) for 24 h at a concentration range of 0-30 µM (zinc) and 0-40 µM (SFN), respectively.

The results showed that in PC-3 cells, the 50% inhibitory concentration ($IC_{50}$) values were 16.2±0.9 µM in response to zinc treatment (FIG. 1A) and 20.3±0.8 µM for SFN (FIG. 1B). In contrast, HPR-1 cells were much insensitive to both treatments, especially to zinc. As shown in FIG. 1A at higher zinc concentration (30 µM), less than 20% of PC-3 cells could survive, while around 90% of HPR-1 cells were still able to stay alive, which are congruent with our previously observations [1,2]. As to SFN treatment HPR-1 cells appeared to be no response to lower concentration of SFN(<10 µM); while at the range of 10 to 25 the proliferation of HPR-1 cells was inhibited in a dose-dependent pattern, although the inhibitory was less effective than that in PC-3 cells. HPR-1 cells appeared to be insensitive and tolerant to SFN at higher concentration (>25 µM), at that condition and reached its plateau at the concentration of 25 µM and even higher. 60% of HPR-1 cells were still alive, while PC-3 cell growth was continuously to be inhibited.

Dose-response study of zinc/SFN combinations and a computerized program analysis to identify the synergistic effect of the combinations in corresponding to their growth inhibitory effect in PC-3 cells Based on the inhibitory effect of zinc and SFN on malignant PC-3 cell growth revealed in FIG. 1, a dose-response study of zinc and SFN with selected dose combinations was carried out to identify if the combinations with selective dosages would play a synergistic effect, which leads to enhanced anti-growth role with reduced dosage to limit the possible toxic effect of the agents.

Table 1 showed that total 21 combinations of zinc and SFN were chosen based on the maximum-power design, the elected concentrations range in zinc (0.42 µM to 22.92 µM) and in SFN (0.66 µM to 30.50 µM). The growth inhibitory effect of these combinations was examined in PC-3 cells and the cell viability was measured by MTT assay. Within total 147 analytic experiments the cell viabilities in response to corresponding combination of zinc and SFN were extended from 71.3% to 31.0% listed in Table 1.

To further characterize the synergistic effect displayed by the combinations of zinc and SFN, a computerized analysis with special analytic program was engaged. FIG. 2A showed the response surface of the combinations of zinc and SFN and the corresponding contour plot is given in FIG. 2B. With the 147 observations from the combination experiments, the F-test proposed by Fang et al. (2003) indicates the definitive area limited to additive effect of zinc and SFN ($F_{19, 126}$=166.4705, p-value <0.0001). Using two dimensional B-spline method (Fang, et al. 2008), we obtained the estimated interaction index surface of zinc and SFN and its contour plot as indicated in FIG. 2C. Each line represents different interaction index value, alone which all corresponding combinations have the same interaction index value. It showed that the combination of zinc and SFN is synergistic at both lower and higher concentrations of zinc and SFN, whereas the additive/antagonism effect was limited to the area corresponding to middle concentrations of each compound.

To select proper combinations of zinc and SFN, FIG. 2B and FIG. 2C were overlaid to generate FIG. 2D, from which six combinations with individual corresponding interaction index less than 1 were selected (zinc & SFN), i.e., 8 μM&20 μM, 10 μM&10 μM, 10 μM&15 μM, 10 μM&20 μM, 15 μM&5 μM and 12.5 μM& 12 μM. The zinc and SFN combinations with these compositions were used as the candidates in further synergistic effect studies.

Synergistic Growth Inhibitory Effect of Zinc and SFN on PC-3 Cells

Synergistic growth inhibitory effect was further characterized in HPR-1 and PC-3 cells (FIG. 3). For each of 6 selected dose combinations, the cells were treated without or with zinc, SFN, respectively, for 24 h, and then the cell viability was assessed using MTT staining. FIG. 3A showed that in HPR-1 cells there were no more than 10 to 20% cell reductions observed with the combinations, and the cells basically have no response to zinc, which was the same to the earlier observation. In contrast, a significant synergistic growth inhibitory effect was observed in PC-3 cells (FIG. 3B). There was more than 70% reduction of cell population when the combination of zinc (12.5 μM) and SFN (12 μM) or with the combination of (10 μM & 15 μM) was applied, in comparison with the 20-30% reduction observed with their individual treatment. The results are consistent with what were predicted in FIG. 2D. Among the 6 combinations, the combination of 12.5 μM zinc and 12 μM SFN has an interaction index less than 0.8 and exhibits maximum synergistic inhibitory effect with considerable reduction of their individual doses (about 20% reduction of zinc and 40% of SFN) to minimize their possible toxic effect we well. This combination elected in the following experiments to study the underlying mechanism(s).

Characterization of Apoptotic Effect Induced by Zinc/SFN Combination in PC-3 Cells Zinc, at a higher concentration, induced prostate cell apoptosis has been reported previously by our group and others. In this study, we further investigated whether the combination of zinc (12.5 μM) and SFN (12 μM) would induce apoptosis in PC-3 cells. Key component proteins involved in zinc induced apoptosis were examined by Western blot (FIG. 4A). Results showed that only the combination of zinc and SFN significantly induced mitochondrial cytochrome c release, which further triggered downstream pro-caspase 3 and PARP (Poly (ADP-ribose) polymerase) activation, evident with the protein cleavage by decreasing levels of the pro-forms (FIG. 4A). The synergistic apoptotic effect was aberrant in comparison to lack of cell responses to either zinc or SFN, respectively.

To further confirm the zinc/SFN combination induced apoptotic characteristics in PC-3 cells, the terminal deoxynucleotidyl transferase dUTP nick end labeling (TUNEL) assay was performed and the results are shown in FIG. 4B. PC-3 cells with different treatments were subjected to Hoechst 33258 and TUNEL staining for individual determination of apoptosis index. With Hoechst staining (blue), nuclear condensation and lower cell density were observed in PC-3 cells treated with zinc/SFN combination compared with other treatments. Correspondingly, many cells with positive TUNEL staining (green) were appeared concordantly only in cells with condensed nuclei, indicating more cells has undergone apoptosis after combined treatment with zinc and SFN.

Synergistic Effect of Zinc/SFN Combination on Stimulating ROS Production in PC-3 Cells, which can be Inhibited by ROS Inhibitors of NAC and GSH Previous studies indicated ROS production involved in both zinc and SFN induced cell apoptosis [3,4], herein we examined the effect of zinc/SFN combination on ROS production in both PC-3 and HPR-1 cells (FIG. 5). The results shown in FIG. 5A demonstrated that in PC-3 cells a dramatic increase of ROS production, about 3 fold increase than that in control, was only observed in the cells treated with zinc/SFN combination after 12 to 24 h. SFN alone increased ROS levels about 35% and 55% and zinc treatment appeared to have less than 40-50% increase of ROS level at the late time points (12 to 24 h). However, in HPR-1 cells a similar steady induction of ROS levels by about 1.5 to 1.8 increase was observed in the cells treated with either SFN or zinc/SFN combination. Neither much higher ROS production, nor synergistic induction effect by zinc/SFN combination was observed. The ROS production in PC-3 cells was further determined by flow cytometry analysis with the cells stained with both PI and DCFDA (FIG. 5B). Results showed that increased cell population exhibiting enhanced fluoresces staining with DCFDA staining (monitoring the ROS production) and with lower staining of PI (indicating a living cell) was only observed in the cells treated with zinc/SFN combination, as shown in lower right area of the corresponding panel in FIG. 5 B. The result indicated that increased ROS production came from living PC-3 cells treated with the combination, but not from the dead cells.

The synergistic effect of zinc/SFN on ROS production in PC-3 cells was further studies using ROS inhibitors of 6 mM N-Acetyl Cysteine (NAC) or reduced glutathionein (GSH) (FIG. 5C). Results showed that both NAC (6 mM) and GSH (6 mM) significantly inhibited ROS production by zinc, SFN or zinc/SFN combination at different time points, The surge of ROS induced by zinc/SFN combination was completely abolished at 24 h of treatment (FIG. 5C). The growth inhibitory effect of zinc, SFN and their combination on PC-3 cell growth was concordantly abolished by NAC and GSH as measured by MTT assay (FIG. 5D).

Synergistic Effect of Zinc/SFN Combination on Losing Mitochondrial Membrane Potential (MMP) Detected in PC-3 Cells It has been long recognized that MMP alteration is one of the major causes of apoptosis. To determine the role of zinc/SFN combination on MMP DIOC6(3) and PI was employed to measure MMP by flow cytometry analysis. As shown in FIG. 6A, zinc/SFN combination exhibited a strong potency on MMP alteration with a time-dependent pattern and the maximum of about 50% of cell population with loss of MMP in comparing to the control (about 10% loss) was reached at 24 h. Interestingly, zinc alone can increase one fold of cell population with loss of MMP than that in the control; and SFN alone, at least at the concentration of 12 μM, did not affect MMP at all. The synergistic effect of zinc/SFN on MMP alteration was completely prevented by pretreatment with NAC and GSH in all groups with different treatment for 24 (FIG. 6B).

Zinc/SFN Combination Significantly Attenuates MT1/2 Protein Levels in PC-3 Cells, but not in HPR-1 Cells MT1/2 proteins are known to be induced by zinc treatment (Hua2008) and MTs are important to cellular zinc homeostasis and function as ROS scavenger, to further understand the relationship between MT expressions and zinc in the presence of SFN we examined MT1/2 levels in PC-3 and HPR-1 cells with the same treatments as described above (FIG. 7). In PC-3 cells (FIG. 7A), a significant induction of MT1/2 was triggered by zinc alone at 24 h, which was as the same as we reported earlier (Hua, 2008), however, SFN alone has no effect or a slight inhibition on MT expression at 6 and 24 h, respectively. Surprisingly, a significant attenuation of MT1/2 levels was observed in the cells treated with zinc/SFN combination in both 6 and 24 h of the treatment. The potency of the suppression in MT1/2 expression by zinc/SFN combination was obviously observed in comparison to the dramatic induction of MT1/2 induced by zinc alone after 24 h treatment. Our result indicated that SFN may play a suppression role to MT1/2 protein levels in PC-3 cells at present condition.

The effect of SFN on MT1/2 was further examined in HPR-1 cells that have been identified to contain much higher endogenous MT1/2 levels than PC-3 cells (Hua2008). As showed in FIG. 7B, zinc alone was also able to induce expression of MT1/2 significantly at 24 h treatment, while SFN decreased expression of MT1/2 comparing to the control at both 6 h and 24 h after treatment. However, the potency of zinc/SFN combination on suppression MT1/2 protein level was less than that in PC-3 cells.

Effect of Zinc/SFN Combination on MAPK Signaling Pathway in PC-3 Cells

MAPK pathway is known to be involved in the machinery mechanism of cell death, to determine whether zinc/SFN combination is able to affect MAPKs, we examined the activation status of three major targets in MAPK subfamilies, i.e., p38, ERK and JNK, in PC-3 cells. FIG. 8A shows that at 6 h treatment, zinc and SFN, respectively, increased phosphorylation of p38, comparing to the control; while zinc/SFN combination synergistically promoted phosphorylation of p38 as well as the activation of ERK. After 24 h treatment, phosphorylated p38 levels in all treatments returned to the control level, while phosphorylation of ERK in cells treated with the combination remained at higher level, compared to the control. In contrast, no alteration of JNK phosphorylation was detected. To identify the earlier activation of p38, a time course study (0.5, 1, 3 and 6 h) was performed in PC-3 cells treated with zinc/SFN combination only (FIG. 8B). Our results showed that the activation of p38 could be detected as early as at 1 h treatment, and continuously increased up to 6 h indicating the fast activation effect of zinc/SFN combination on p38.

Pharmaceutical Compositions and Dosage Forms

Pharmaceutical compositions can be used in the preparation of individual dosage forms. Pharmaceutical compositions and dosage forms of the invention comprise the active ingredients disclosed herein (e.g., SFN or a pharmaceutically acceptable prodrug, salt, solvate, or hydrate thereof). Pharmaceutical compositions and dosage forms of the invention can further comprise one or more excipients.

Pharmaceutical compositions and dosage forms of the invention can also comprise one or more additional active ingredients. Single unit dosage forms of the invention are suitable for oral, mucosal, parenteral, intravenous or transdermal administration to a patient. Examples of dosage forms include, but are not limited to: tablets, caplets, capsules, cachets, troches, lozenges, dispersions, suppositories, ointments, pastes, powders, creams, solutions, patches, gels, and pumped directly to solid tumors.

The composition, shape, and type of dosage forms of the invention will typically vary depending on their use. For example, a dosage form used in the treatment of a disease may contain larger amounts of one or more of the active ingredients it comprises than a dosage form used in the chronic treatment of the same disease. A parenteral dosage form may contain smaller amounts of one or more of the active ingredients it comprises than an oral dosage form used to treat the same disease. These and other ways in which specific dosage forms encompassed in this invention will vary from one another will be readily apparent to those skilled in the art. See e.g, *Remington's Pharmaceutical Sciences*, $18^{th}$ ed., Mack Publishing, Easton, Pa. (1990).

Examples of commercially available forms of zinc include but are not limited to: zinc chloride, zinc sulfate, and zinc gluconate. One commonly used source of SFN is sulforaphane glucosinate.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art.

Like the amounts of types of excipients, the amounts and specific types of active ingredients in dosage form may differ depending on factors such as, but not limited to, the route by which it is to be administered to patients. However, typical dosage forms of the invention comprise SFN, a derivative or analog of SFN, or a pharmaceutically acceptable salt, hydrate or prodrug in an amounts ranging from milligram to gram levels. Zinc dosage levels can range from about 15 to about 100 mg/day, administered orally. Zinc can also be administered via other routes of administration at dosages which can readily be determined by one of ordinary skill in the art.

Pharmaceutical compositions of the invention that are suitable for oral administration can be presented as discrete dosage forms, such as, but are not limited to tablets, caplets, capsules and liquids. Such dosage forms contain predetermined amounts of active ingredients and may be prepared by methods of pharmacy well known to those skilled in the art. See e.g., Remington's Pharmaceutical Sciences, $18^{th}$ ed., Mack Publishing, Easton, Pa. (1990).

Active ingredients of the invention can be administered by controlled release means or by delivery devices that are well known to those of ordinary skill in the art. Examples include, but are not limited to those described in U.S. Pat Nos.: 3,845,770; 3,598,123; 3,916,899; 4,008,719; 5,674,533; 5,591,767; 5,639,476, 5,354,556; and 5,733,566, each of which is incorporated herein by reference. The invention thus encompasses single unit dosage forms suitable for oral administration such as but not limited to tablets, capsules, gelcaps, and caplets that are adapted for controlled-release.

Kits

The active ingredients of the invention may not necessarily be administered to a patient at the same time or via the same route of administration. This invention therefore encompasses kits which, when used by the medical practitioner, can simplify the administration of appropriate amounts of active ingredients to a patient.

A typical kit of the invention comprises a dosage form of SFN or a pharmaceutically acceptable prodrug, salt or hydrate thereof and a dosage form of zinc or a pharmaceutically acceptable salt or derivative thereof. Kits encompassed by this invention can further comprise additional active ingredients, e.g. selenium.

Kits of the invention can further comprise devices that are used to administer the active ingredients. Examples of such devices include: but are not limited to: oral, drip bags, patches, and inhalers or application of the active ingredients directly to the tumor.

REFERENCES

1. Gayathri R, Gunadharini D N, Arunkumar A, Senthilkumar K, Krishnamoorthy G, Banudevi S et al.: Effects of diallyl disulfide (DADS) on expression of apoptosis associated proteins in androgen independent human prostate cancer cells (PC-3). *Mol Cell Biochem* 2008.
2. Gronberg H: Prostate cancer epidemiology. *Lancet* 2003, 361: 859-864.
3. Syed D N, Suh Y, Afaq F, Mukhtar H: Dietary agents for chemoprevention of prostate cancer. *Cancer Lett* 2008, 265: 167-176.
4. Jemal A, Siegel R, Ward E, Murray T, Xu J, Thun M J: Cancer statistics, 2007. *CA Cancer J Clin* 2007, 57: 43-66.
5. Moon C, Park J C, Chae Y K, Yun J H, Kim S: Current status of experimental therapeutics for prostate cancer. *Cancer Lett* 2008, 266: 116-134.
6. Frassinetti S, Bronzetti G, Caltavuturo L, Cini M, Croce C D: The role of zinc in life: a review. *J Environ Pathol Toxicol Oncol* 2006, 25: 597-610.
7. Sekler I, Sensi S L, Hershfmkel M, Silverman W F: Mechanism and regulation of cellular zinc transport. *Mol Med* 2007, 13: 337-343.
8. Yamasaki S, Sakata-Sogawa K, Hasegawa A, Suzuki T, Kabu K, Sato E et al.: Zinc is a novel intracellular second messenger. *J Cell Biol* 2007, 177: 637-645.
9. Costello L C, Franklin R B: Novel role of zinc in the regulation of prostate citrate metabolism and its implications in prostate cancer. *Prostate* 1998, 35: 285-296.
10. Wei H, Desouki M M, Lin S, Xiao D, Franklin R B, Feng P: Differential expression of metallothioneins (MTs) 1, 2, and 3 in response to zinc treatment in human prostate normal and malignant cells and tissues. *Mol Cancer* 2008, 7: 7.
11. Feng P, Li T, Guan Z, Franklin R B, Costello L C: The Involvement of Bax in Zinc-Induced Mitochondrial Apoptogenesis in Malignant Prostate Cells. *Mol Cancer* 2008, 7: 25.
12. Feng P, Li T L, Guan Z X, Franklin R B, Costello L C: Direct effect of zinc on mitochondrial apoptogenesis in prostate cells. *Prostate* 2002, 52: 311-318.
13. Feng P, Liang J Y, Li T L, Guan Z X, Zou J, Franklin R et al.: Zinc induces mitochondria apoptogenesis in prostate cells. *Mol Urol* 2000, 4: 31-36.
14. Joseph M A, Moysich K B, Freudenheim J L, Shields P G, Bowman E D, Zhang Y et al.: Cruciferous vegetables, genetic polymorphisms in glutathione S-transferases M1 and T1, and prostate cancer risk. *Nutr Cancer* 2004, 50: 206-213.
15. Giovannucci E, Rimm E B, Liu Y, Stampfer M J, Willett W C: A prospective study of cruciferous vegetables and prostate cancer. *Cancer Epidemiol Biomarkers Prev* 2003, 12: 1403-1409.
16. Cohen J H, Kristal A R, Stanford J L: Fruit and vegetable intakes and prostate cancer risk. *J Natl Cancer Inst* 2000, 92: 61-68.
17. Zhang Y, Talalay P, Cho C G, Posner G H: A major inducer of anticarcinogenic protective enzymes from broccoli: isolation and elucidation of structure. *Proc Natl Acad Sci USA* 1992, 89: 2399-2403.
18. Juge N, Mithen R F, Traka M: Molecular basis for chemoprevention by sulforaphane: a comprehensive review. *Cell Mol Life Sci* 2007, 64: 1105-1127.
19. Jin C Y, Moon D O, Lee J D, Heo M S, Choi Y H, Lee C M et al.: Sulforaphane sensitizes tumor necrosis factor-related apoptosis-inducing ligand-mediated apoptosis through downregulation of ERK and Akt in lung adenocarcinoma A549 cells. *Carcinogenesis* 2007, 28: 1058-1066.
20. Kim H, Kim E H, Eom Y W, Kim W H, Kwon T K, Lee S J et al.: Sulforaphane sensitizes tumor necrosis factor-related apoptosis-inducing ligand (TRAIL)-resistant hepatoma cells to TRAIL-induced apoptosis through reactive oxygen species-mediated up-regulation of DR5. *Cancer Res* 2006, 66: 1740-1750.
21. Chen Q, Gong B, Almasan A: Distinct stages of cytochrome c release from mitochondria: evidence for a feedback amplification loop linking caspase activation to mitochondrial dysfunction in genotoxic stress induced apoptosis. *Cell Death Differ* 2000, 7: 227-233.
22. Feng P, Liang J Y, Li T L, Guan Z X, Zou J, Franklin R et al.: Zinc induces mitochondria apoptogenesis in prostate cells. *Mol Urol* 2000, 4: 31-36.
23. Feng P, Li T L, Guan Z X, Franklin R B, Costello L C: Direct effect of zinc on mitochondrial apoptogenesis in prostate cells. *Prostate* 2002, 52: 311-318.
24. Fang H B, Ross D D, Sausville E, Tan M: Experimental design and interaction analysis of combination studies of drugs with log-linear dose responses. *Stat Med* 2008.
25. Feng P, Li T L, Guan Z X, Franklin R B, Costello L C: Direct effect of zinc on mitochondrial apoptogenesis in prostate cells. *Prostate* 2002, 52: 311-318.
26. Singh S V, Srivastava S K, Choi S, Lew K L, Antosiewicz J, Xiao D et al.: Sulforaphane-induced cell death in human prostate cancer cells is initiated by reactive oxygen species. *J Biol Chem* 2005, 280: 19911-19924.
27. Myzak M C, Hardin K, Wang R, Dashwood R H, Ho E: Sulforaphane inhibits histone deacetylase activity in BPH-1, LnCaP and PC-3 prostate epithelial cells. *Carcinogenesis* 2006, 27: 811-819.
28. Choi S, Lew K L, Xiao H, Herman-Antosiewicz A, Xiao D, Brown C K et al.: D,L-Sulforaphane-induced cell death in human prostate cancer cells is regulated by inhibitor of apoptosis family proteins and Apaf-1. *Carcinogenesis* 2007, 28: 151-162.
29. Choi S, Singh S V: Bax and Bak are required for apoptosis induction by sulforaphane, a cruciferous vegetable-derived cancer chemopreventive agent. *Cancer Res* 2005, 65: 2035-2043.
30. Nair S, Hebbar V, Shen G, Gopalakrishnan A, Khor T O, Yu S et al.: Synergistic effects of a combination of dietary factors sulforaphane and (−) epigallocatechin-3-gallate in HT-29 AP-1 human colon carcinoma cells. *Pharm Res* 2008, 25: 387-399.
31. Pappa G, Strathmann J, Lowinger M, Bartsch H, Gerhauser C: Quantitative combination effects between sulforaphane and 3,3'-diindolylmethane on proliferation of human colon cancer cells in vitro. *Carcinogenesis* 2007, 28: 1471-1477.
32. Svehlikova V, Wang S, Jakubikova J, Williamson G, Mithen R, Bao Y: Interactions between sulforaphane and apigenin in the induction of UGT1A1 and GSTA1 in CaCo-2 cells. *Carcinogenesis* 2004, 25: 1629-1637.
33. Mabjeesh N J, Willard M T, Harris W B, Sun H Y, Wang R, Thong H et al.: Dibenzoylmethane, a natural dietary compound, induces HIF-1 alpha and increases expression of VEGF. *Biochem Biophys Res Commun* 2003, 303: 279-286.

34. Singh A V, Xiao D, Lew K L, Dhir R, Singh S V: Sulforaphane induces caspase-mediated apoptosis in cultured PC-3 human prostate cancer cells and retards growth of PC-3 xenografts in vivo. *Carcinogenesis* 2004, 25: 83-90.

35. Gazarykov I G, Krasnikov B F, Ashby G A, Thomeley R N, Kristal B S, Brown A M: Zinc is a potent inhibitor of thiol oxidoreductase activity and stimulates reactive oxygen species production by lipoamide dehydrogenase. *J Biol Chem* 2002, 277: 10064-10072.

36. Bishop G M, Dringen R, Robinson S R: Zinc stimulates the production of toxic reactive, oxygen species (ROS) and inhibits glutathione reductase in astrocytes. *Free Radic Biol Med* 2007, 42: 1222-1230.

37. Gazarykov I G, Krasinskaya I P, Kristal B S, Brown A M: Zinc irreversibly damages major enzymes of energy production and antioxidant defense prior to mitochondrial permeability transition. *J Biol Chem* 2007, 282: 24373-24380.

38. Donadelli M, Dalla P E, Scupoli M T, Costanzo C, Scarpa A, Palmieri M: Intracellular zinc increase inhibits p53(-/-) pancreatic adenocarcinoma cell growth by ROS/AIF-mediated apoptosis: *Biochim Biophys Acta* 2008.

39. Rudolf E, Rudolf K, Cervinka M: Zinc induced apoptosis in HEP-2 cancer cells: the role of oxidative stress and mitochondria. *Biofactors* 2005, 23: 107-120.

40. Shankar S, Ganaphthy S, Srivastava R K: Sulforaphane Enhances the Therapeutic Potential of TRAIL in Prostate Cancer Orthotopic Model through Regulation of Apoptosis, Metastasis, and Angiogenesis. *Clin Cancer Res* 2008, 14: 6855-6866.

41. Moon D O, Kim M O, Kang S H, Choi Y H, Kim G Y: Sulforaphane suppresses TNF-alpha-mediated activation of NF-kappaB and induces apoptosis through activation of reactive oxygen species-dependent caspase-3. *Cancer Lett* 2008.

42. Choi W Y, Choi B T, Lee W H, Choi Y H: Sulforaphane generates reactive oxygen species leading to mitochondrial perturbation for apoptosis in human leukemia U937 cells. *Biomed Pharmacother* 2008.

43. Fagian M M, Pereira-da-Silva L, Martins I S, Vercesi A E: Membrane protein thiol cross-linking associated with the permeabilization of the inner mitochondrial membrane by Ca2+ plus prooxidants. *J Biol Chem* 1990, 265: 19955-19960.

44. Castilho R F, Kowaltowski A J, Meinicke A R, Bechara E J, Vercesi A E: Permeabilization of the inner mitochondrial membrane by Ca2+ ions is stimulated by t-butyl hydroperoxide and mediated by reactive oxygen species generated by mitochondria. *Free Radic Biol Med* 1995, 18: 479-486.

45. Sumbayev V V, Yasinska I M: Regulation of MAP kinase-dependent apoptotic pathway: implication of reactive oxygen and nitrogen species. *Arch Biochem Biophys* 2005, 436: 406-412.

46. Takeda K, Matsuzawa A, Nishitoh H, Ichijo H: Roles of MAPKKK ASK1 in stress-induced cell death. *Cell Struct Funct* 2003, 28: 23-29.

47. Baines C P, Molkentin J D: STRESS signaling pathways that modulate cardiac myocyte apoptosis. *J Mol Cell Cardiol* 2005, 38: 47-62.

48. Raman M, Chen W, Cobb M H: Differential regulation and properties of MAPKs. *Oncogene* 2007, 26: 3100-3112.

49. Zhuang S, Demirs J T, Kochevar I E: p38 mitogen-activated protein kinase mediates bid cleavage, mitochondrial dysfunction, and caspase-3 activation during apoptosis induced by singlet oxygen but not by hydrogen peroxide. *J Biol Chem* 2000, 275: 25939-25948.

50. Huot J, Houle F, Marceau F, Landry J: Oxidative stress-induced actin reorganization mediated by the p38 mitogen-activated protein kinase/heat shock protein 27 pathway in vascular endothelial cells. *Circ Res* 1997, 80: 383-392.

51. Van D R, Xue Y, Knudson A, Pelling J C: The chemopreventive bioflavonoid apigenin modulates signal transduction pathways in keratinocyte and colon carcinoma cell lines. *J Nutr* 2003, 133: 3800S-3804S.

52. Thirumoorthy N, Manisenthil Kumar K T, Shyam S A, Panayappan L, Chatterjee M: Metallothionein: an overview. *World J Gastroenterol* 2007, 13: 993-996.

53. Yeh C T, Yen G C: Effect of sulforaphane on metallothionein expression and induction of apoptosis in human hepatoma HepG2 cells. *Carcinogenesis* 2005, 26: 2138-2148.

54. Yao H, Wang H, Zhang Z, Jiang B H, Luo J, Shi X: Sulforaphane inhibited expression of hypoxia-inducible factor-1alpha in human tongue squamous cancer cells and prostate cancer cells. *Int J Cancer* 2008, 123: 1255-1261.

55. Murphy B J, Kimura T, Sato B G, Shi Y, Andrews G K: Metallothionein induction by hypoxia involves cooperative interactions between metal-responsive transcription factor-1 and hypoxia-inducible transcription factor-1alpha. *Mol Cancer Res* 2008, 6: 483-490.

56. Kroncke K D: Cellular stress and intracellular zinc dyshomeostasis. *Arch Biochem Biophys* 2007, 463: 183-187.

57. Quesada A R, Byrnes R E, Krezoski S O, Petering D H: Direct reaction of H2O2 with sulfhydryl groups in HL-60 cells: zinc-metallothionein and other sites. *Arch Biochem Biophys* 1996, 334: 241-250.

Although the invention has been described in example embodiments, those skilled in the art will appreciate that various modification may be made without departing from the spirit and scope of the invention. It is therefore understood that the invention may be practiced other than as specifically described. Thus, the present embodiments should be considered in all respects as illustrative and not restrictive. Accordingly, it is intended that such changes and modifications fall within the scope of the present invention as defined by the claims appended hereto. All materials referred to herein, including books, manuals, journals, publications, posters, abstracts, talks, patents and published patent applications are incorporated by reference herein in there entireties.

TABLE 1

Twenty-one combinations of zinc and SFN for combination experiment.

| Experiment number | Zinc (μM) | SFN (μM) | Mean Viability (% of control) |
|---|---|---|---|
| Control | 0 | 0 | 100 |
| 1 | 6.49 | 4.38 | 65.50 |
| 2 | 1.41 | 11.50 | 4.00 |
| 3 | 11.86 | 1.07 | 62.09 |
| 4 | 4.86 | 10.71 | 47.85 |
| 5 | 10.66 | 4.76 | 62.96 |
| 6 | 3.26 | 15.40 | 48.81 |
| 7 | 7.25 | 11.46 | 56.11 |
| 8 | 0.42 | 22.78 | 46.32 |
| 9 | 12.66 | 7.57 | 31.99 |
| 10 | 14.00 | 3.69 | 47.03 |
| 11 | 9.55 | 12.76 | 33.11 |
| 12 | 6.14 | 18.33 | 41.70 |
| 13 | 20.12 | 0.66 | 8.84 |
| 14 | 3.56 | 23.74 | 27.52 |
| 15 | 12.13 | 13.31 | 3.33 |
| 16 | 18.00 | 6.49 | 0.53 |
| 17 | 6.20 | 23.01 | 14.25 |
| 18 | 15.72 | 11.44 | 0.02 |
| 19 | 1.80 | 30.50 | 2.71 |
| 20 | 22.92 | 4.01 | 0 |
| 21 | 10.85 | 20.50 | 0 |

What is claimed is:

1. A method for treating prostate cancer which comprises administering to a mammal in need of treatment an effective amount of sulforaphane (SFN) or a pharmaceutically acceptable salt, solvate or hydrate thereof, or sulforaphane glucosinate, and concomitantly administering an effective amount of zinc; wherein the concentration of zinc is 12.5 µM and the concentration of sulforaphane is 12 µM, wherein the concentrations of sulforaphane and zinc exhibit a synergistic growth inhibitory effect on prostate cancer cells in the mammal.

2. The method of claim 1, wherein the mammal is a human.

3. The method of claim 1, wherein the combination treatment of zinc and sulforaphane causes apoptosis of cancer cells.

4. The method of claim 1, wherein the zinc is selected from the group consisting of zinc chloride, zinc sulfate, and zinc gluconate.

* * * * *